(12) United States Patent
Velazquez et al.

(10) Patent No.: US 11,992,382 B2
(45) Date of Patent: May 28, 2024

(54) VIRTUAL FILLERS FOR VIRTUAL MODELS OF DENTAL ARCHES

(71) Applicant: Align Technology, Inc., San Jose, CA (US)

(72) Inventors: Israel Velazquez, Juarez (MX); Andrey Cherkas, Krasnoznamensk (RU); Stephan Albert Alexandre Dumothier, Houston, TX (US); Anatoliy Parpara, Moscow (RU); Alexey Geraskin, Moscow (RU); Yury Slynko, Moscow (RU); Danila Chesnokov, Barnaul (RU)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 17/411,984

(22) Filed: Aug. 25, 2021

(65) Prior Publication Data
US 2021/0378794 A1    Dec. 9, 2021

Related U.S. Application Data

(63) Continuation of application No. 16/936,114, filed on Jul. 22, 2020, now Pat. No. 11,129,694, which is a continuation of application No. 16/151,164, filed on Oct. 3, 2018, now Pat. No. 10,722,328, which is a
(Continued)

(51) Int. Cl.
| | |
|---|---|
| *G06T 15/00* | (2011.01) |
| *A61C 7/00* | (2006.01) |
| *G06T 5/70* | (2024.01) |
| *G06T 17/20* | (2006.01) |

(Continued)

(52) U.S. Cl.
CPC ............... *A61C 7/002* (2013.01); *G06T 5/70* (2024.01); *G06T 17/20* (2013.01); *G06T 17/205* (2013.01); *G06T 19/00* (2013.01); *A61C 2007/004* (2013.01); *G06T 2207/30036* (2013.01); *G06T 2210/36* (2013.01); *G06T 2210/41* (2013.01); *G06T 2210/56* (2013.01); *G16H 50/50* (2018.01)

(58) Field of Classification Search
CPC ........... A61C 7/002; A61C 7/08; A61C 9/004; G06F 30/20
USPC ........................................................ 345/418
See application file for complete search history.

(56) References Cited

U.S. PATENT DOCUMENTS

| | | |
|---|---|---|
| 5,975,893 A | 11/1999 | Chishti et al. |
| 6,227,850 B1 | 5/2001 | Chishti et al. |
| 6,227,851 B1 | 5/2001 | Chishti et al. |

(Continued)

OTHER PUBLICATIONS

Kusalanukhun, Teeraporn, Chanjira Sinthanayothin, and Wichit Tharanon. "An Algorithm of 3D Objects Connection for Dental Bridge Design." (2015).*

(Continued)

*Primary Examiner* — Phu K Nguyen
(74) *Attorney, Agent, or Firm* — Lowenstein Sandler LLP

(57) ABSTRACT

A virtual filler is inserted in a virtual model of a dental site between a first tooth and a second tooth in the virtual model. One or more of the first tooth or the second tooth represent a natural tooth of a patient. Points of the first tooth, the second tooth and the virtual filler are transformed into a voxel volume. A geometry of an updated virtual filler is determined by transforming a surface of the voxel volume into a polygonal mesh.

20 Claims, 27 Drawing Sheets

Related U.S. Application Data continuation-in-part of application No. 15/726,211, filed on Oct. 5, 2017, now Pat. No. 11,033,359.

(51) Int. Cl.
  *G06T 19/00* (2011.01)
  *G16H 50/50* (2018.01)

(56) References Cited

U.S. PATENT DOCUMENTS

| | | |
|---|---|---|
| 6,299,440 B1 | 10/2001 | Phan et al. |
| 6,318,994 B1 | 11/2001 | Chishti et al. |
| 6,371,761 B1 | 4/2002 | Cheang et al. |
| 6,386,878 B1 | 5/2002 | Pavlovskaia et al. |
| 6,406,292 B1 | 6/2002 | Chishti et al. |
| 6,409,504 B1 | 6/2002 | Jones et al. |
| 6,457,972 B1 | 10/2002 | Chishti et al. |
| 6,488,499 B1 | 12/2002 | Miller |
| 6,514,074 B1 | 2/2003 | Chishti et al. |
| 6,554,611 B2 | 4/2003 | Chishti et al. |
| 6,582,229 B1 | 6/2003 | Miller et al. |
| 6,602,070 B2 | 8/2003 | Miller et al. |
| 6,621,491 B1 | 9/2003 | Baumrind et al. |
| 6,688,886 B2 | 2/2004 | Hughes et al. |
| 6,726,478 B1 | 4/2004 | Isiderio et al. |
| 6,729,876 B2 | 5/2004 | Chishti et al. |
| 6,739,869 B1 | 5/2004 | Taub et al. |
| 6,767,208 B2 | 7/2004 | Kaza |
| 6,783,360 B2 | 8/2004 | Chishti |
| 7,040,896 B2 | 5/2006 | Pavlovskaia et al. |
| 7,063,532 B1 | 6/2006 | Jones et al. |
| 7,074,038 B1 | 7/2006 | Miller |
| 7,074,039 B2 | 7/2006 | Kopelman et al. |
| 7,077,647 B2 | 7/2006 | Choi et al. |
| 7,108,508 B2 | 9/2006 | Hedge et al. |
| 7,134,874 B2 | 11/2006 | Chishti et al. |
| 7,156,661 B2 | 1/2007 | Choi et al. |
| 7,160,107 B2 | 1/2007 | Kopelman et al. |
| 7,241,142 B2 | 7/2007 | Abolfathi et al. |
| 7,293,988 B2 | 11/2007 | Wen |
| 7,309,230 B2 | 12/2007 | Wen |
| 7,357,634 B2 | 4/2008 | Knopp |
| 7,555,403 B2 | 6/2009 | Kopelman et al. |
| 7,637,740 B2 | 12/2009 | Knopp |
| 7,689,398 B2 | 3/2010 | Cheng et al. |
| 7,736,147 B2 | 6/2010 | Kaza et al. |
| 7,746,339 B2 | 6/2010 | Matov et al. |
| 7,844,356 B2 | 11/2010 | Matov et al. |
| 7,844,429 B2 | 11/2010 | Matov et al. |
| 7,865,259 B2 | 1/2011 | Kuo et al. |
| 7,878,804 B2 | 2/2011 | Korytov et al. |
| 7,880,751 B2 | 2/2011 | Kuo et al. |
| 7,904,308 B2 | 3/2011 | Arnone et al. |
| 7,930,189 B2 | 4/2011 | Kuo |
| 7,942,672 B2 | 5/2011 | Kuo |
| 7,970,627 B2 | 6/2011 | Kuo et al. |
| 7,970,628 B2 | 6/2011 | Kuo et al. |
| 8,038,444 B2 | 10/2011 | Kitching et al. |
| 8,044,954 B2 | 10/2011 | Kitching et al. |
| 8,075,306 B2 | 12/2011 | Kitching et al. |
| 8,092,215 B2 | 1/2012 | Stone-Collonge et al. |
| 8,099,268 B2 | 1/2012 | Kitching et al. |
| 8,108,189 B2 | 1/2012 | Chelnokov et al. |
| 8,126,726 B2 | 2/2012 | Matov et al. |
| 8,260,591 B2 | 9/2012 | Kass et al. |
| 8,275,180 B2 | 9/2012 | Kuo |
| 8,401,826 B2 | 3/2013 | Cheng et al. |
| 8,439,672 B2 | 5/2013 | Matov et al. |
| 8,562,338 B2 | 10/2013 | Kitching et al. |
| 8,591,225 B2 | 11/2013 | Wu et al. |
| 8,788,285 B2 | 7/2014 | Kuo |
| 8,843,381 B2 | 9/2014 | Kuo et al. |
| 8,874,452 B2 | 10/2014 | Kuo |
| 8,896,592 B2 | 11/2014 | Boltunov et al. |
| 8,930,219 B2 | 1/2015 | Trosien et al. |
| 9,037,439 B2 | 5/2015 | Kuo et al. |
| 9,060,829 B2 | 6/2015 | Sterental et al. |
| 9,125,709 B2 | 9/2015 | Matty |
| 9,211,166 B2 | 12/2015 | Kuo et al. |
| 9,220,580 B2 | 12/2015 | Borovinskih et al. |
| 9,375,300 B2 | 6/2016 | Matov et al. |
| 9,414,897 B2 | 8/2016 | Wu et al. |
| 9,492,245 B2 | 11/2016 | Sherwood et al. |
| 9,642,678 B2 | 5/2017 | Kuo |
| 10,248,883 B2 | 4/2019 | Borovinskih et al. |
| 10,342,638 B2 | 7/2019 | Kitching et al. |
| 10,463,452 B2 | 11/2019 | Matov et al. |
| 10,595,966 B2 | 3/2020 | Carrier, Jr. et al. |
| 10,617,489 B2 | 4/2020 | Grove et al. |
| 10,758,322 B2 | 9/2020 | Pokotilov et al. |
| 10,779,718 B2 | 9/2020 | Meyer et al. |
| 10,792,127 B2 | 10/2020 | Kopelman et al. |
| 10,828,130 B2 | 11/2020 | Pokotilov et al. |
| 10,835,349 B2 | 11/2020 | Cramer et al. |
| 10,973,611 B2 | 4/2021 | Pokotilov et al. |
| 10,996,813 B2 | 5/2021 | Makarenkova et al. |
| 10,997,727 B2 | 5/2021 | Xue et al. |
| 11,020,205 B2 | 6/2021 | Li et al. |
| 11,020,206 B2 | 6/2021 | Shi et al. |
| 11,026,766 B2 | 6/2021 | Chekh et al. |
| 11,033,359 B2 | 6/2021 | Velazquez et al. |
| 11,071,608 B2 | 7/2021 | Derakhshan et al. |
| 11,096,763 B2 | 8/2021 | Akopov et al. |
| 11,116,605 B2 | 9/2021 | Nyukhtikov et al. |
| 11,147,652 B2 | 10/2021 | Mason et al. |
| 11,151,753 B2 | 10/2021 | Gao et al. |
| 2003/0008259 A1 | 1/2003 | Kuo et al. |
| 2003/0143509 A1 | 7/2003 | Kopelman et al. |
| 2003/0207227 A1 | 11/2003 | Abolfathi |
| 2004/0137400 A1 | 7/2004 | Chishti et al. |
| 2004/0152036 A1 | 8/2004 | Abolfathi |
| 2004/0197728 A1 | 10/2004 | Abolfathi et al. |
| 2004/0229183 A1 | 11/2004 | Knopp et al. |
| 2004/0259049 A1 | 12/2004 | Kopelman et al. |
| 2005/0128211 A1* | 6/2005 | Berger .................. G06T 15/04 345/582 |
| 2005/0182654 A1 | 8/2005 | Abolfathi et al. |
| 2005/0244791 A1 | 11/2005 | Davis et al. |
| 2006/0127836 A1 | 6/2006 | Wen |
| 2006/0127852 A1 | 6/2006 | Wen |
| 2006/0127854 A1 | 6/2006 | Wen |
| 2006/0275731 A1 | 12/2006 | Wen et al. |
| 2006/0275736 A1 | 12/2006 | Wen et al. |
| 2008/0220395 A1 | 9/2008 | Marshall et al. |
| 2008/0306724 A1 | 12/2008 | Kitching et al. |
| 2009/0248184 A1* | 10/2009 | Steingart ............... A61C 1/084 700/98 |
| 2010/0009308 A1 | 1/2010 | Wen et al. |
| 2010/0068672 A1 | 3/2010 | Arjomand et al. |
| 2010/0068676 A1 | 3/2010 | Mason et al. |
| 2010/0092907 A1 | 4/2010 | Knopp |
| 2010/0138025 A1* | 6/2010 | Morton ................... G06F 30/00 700/103 |
| 2010/0167243 A1 | 7/2010 | Spiridonov et al. |
| 2011/0091832 A1* | 4/2011 | Kim ...................... B33Y 80/00 700/119 |
| 2013/0204599 A1 | 8/2013 | Matov et al. |
| 2014/0142897 A1* | 5/2014 | Kuo ...................... G16H 50/50 703/1 |
| 2016/0135925 A1 | 5/2016 | Mason et al. |
| 2016/0242870 A1 | 8/2016 | Matov et al. |
| 2016/0310235 A1 | 10/2016 | Derakhshan et al. |
| 2017/0273760 A1 | 9/2017 | Morton et al. |
| 2018/0153648 A1* | 6/2018 | Shanjani ............... B33Y 50/02 |
| 2018/0280118 A1 | 10/2018 | Cramer |
| 2019/0029784 A1 | 1/2019 | Moalem et al. |
| 2019/0053876 A1 | 2/2019 | Sterental et al. |
| 2019/0102880 A1* | 4/2019 | Parpara ................. G06T 17/10 |
| 2019/0192259 A1 | 6/2019 | Kopelman et al. |
| 2019/0328487 A1 | 10/2019 | Levin et al. |
| 2019/0328488 A1 | 10/2019 | Levin et al. |
| 2019/0333622 A1 | 10/2019 | Levin et al. |
| 2019/0343601 A1 | 11/2019 | Roschin et al. |
| 2020/0000552 A1 | 1/2020 | Mednikov et al. |

(56) References Cited

U.S. PATENT DOCUMENTS

| | | |
|---|---|---|
| 2020/0000554 A1 | 1/2020 | Makarenkova et al. |
| 2020/0000555 A1 | 1/2020 | Yuryev et al. |
| 2020/0085546 A1 | 3/2020 | Li et al. |
| 2020/0105028 A1 | 4/2020 | Gao et al. |
| 2020/0107915 A1 | 4/2020 | Roschin et al. |
| 2020/0155274 A1 | 5/2020 | Pimenov et al. |
| 2020/0214800 A1 | 7/2020 | Matov et al. |
| 2020/0297458 A1 | 9/2020 | Roschin et al. |
| 2020/0306011 A1 | 10/2020 | Chekhonin et al. |
| 2020/0306012 A1 | 10/2020 | Roschin et al. |
| 2020/0315744 A1 | 10/2020 | Cramer |
| 2020/0360109 A1 | 11/2020 | Gao et al. |
| 2021/0073998 A1 | 3/2021 | Brown et al. |
| 2021/0134436 A1 | 5/2021 | Meyer et al. |
| 2021/0174477 A1 | 6/2021 | Shi et al. |

OTHER PUBLICATIONS

Majenta Solutions, SensAble FreeForm Modelling Plus—Modelling a Shoe Sole, Jul. 31, 2009; https://www.youtube.com/watch?v=NxhYux7hYGQ.*

Chang M, Oh JW, Chang DS, Park SC. Interactive marching cubes algorithm for intraoral scanners. International Journal of Advanced Manufacturing Technology. Aug. 6, 2016:1-0.*

\* cited by examiner

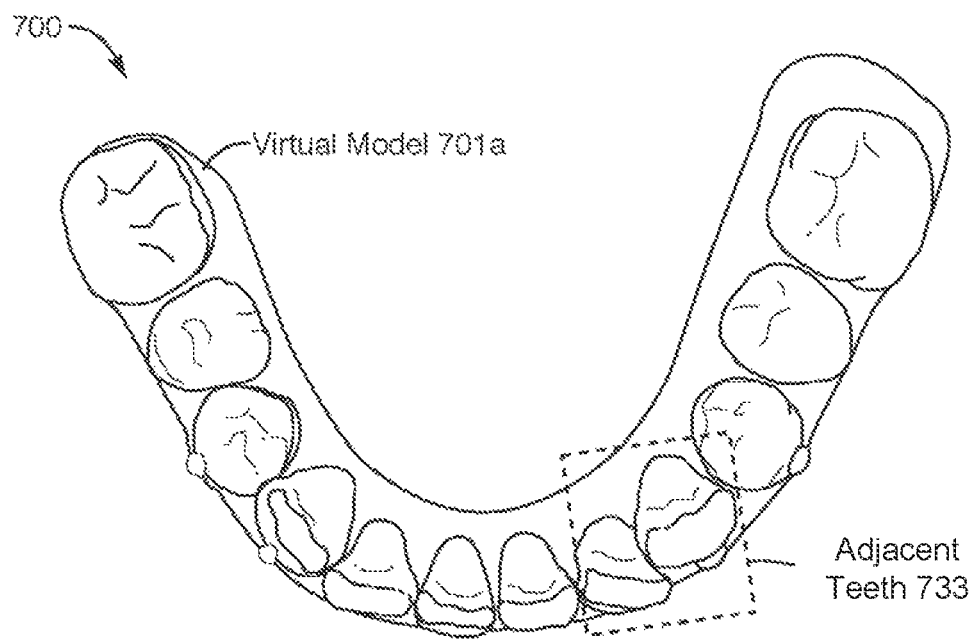
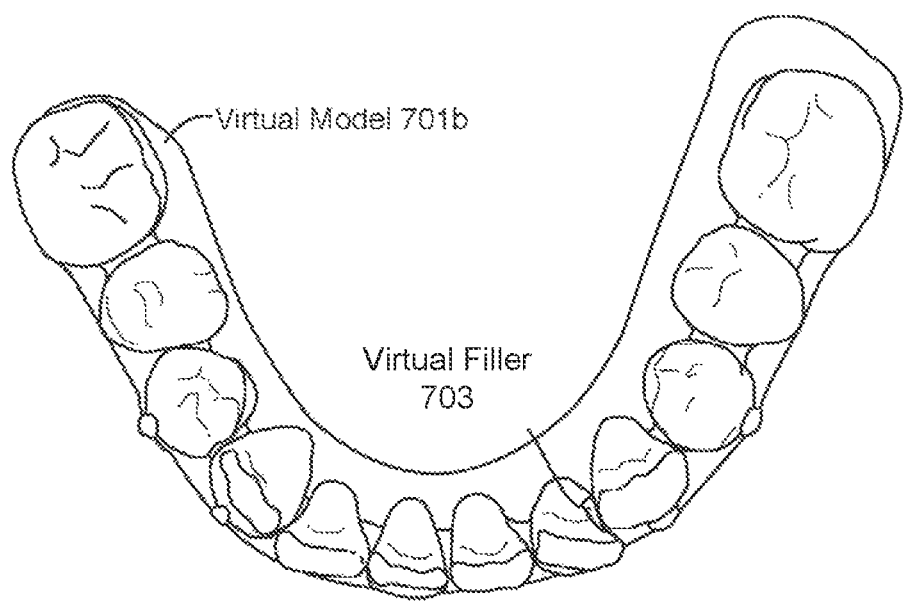
FIG. 7

VIRTUAL FILLERS FOR VIRTUAL MODELS OF DENTAL ARCHES

RELATED APPLICATIONS

This application is a continuation of U.S. patent application Ser. No. 16/936,114, filed Jul. 22, 2020, which is a continuation of U.S. patent application Ser. No. 16/151,164, filed Oct. 3, 2018, issued as U.S. Pat. No. 10,722,328, which is a continuation-in-part application of U.S. patent application Ser. No. 15/726,211, filed Oct. 5, 2017, issued as U.S. Pat. No. 11,033,359, the entire contents of all are hereby incorporated by reference herein.

TECHNICAL FIELD

Embodiments of the present disclosure relate to the field of orthodontics and, in particular, to digital models of dental arches used for the manufacturing of orthodontic aligners.

BACKGROUND

Orthodontic procedures typically involve repositioning a patient's teeth to a desired arrangement in order to correct malocclusions or improve aesthetics. To achieve these objectives, orthodontic appliances such as braces, retainers, aligners, and the like can be applied to the patient's teeth by an orthodontic practitioner. The appliance is configured to exert force on one or more teeth in order to effect desired tooth movements. The application of force can be periodically adjusted by the practitioner (e.g., by altering the appliance or using different types of appliances) in order to incrementally reposition the teeth to a desired arrangement.

A polymeric orthodontic aligner may be formed to fit over a patient's teeth. However, in some instances features of the patient's teeth and/or attachments on the patient's teeth may make it difficult for the patient to put on and/or take off an aligner. Additionally, such features and/or attachments may cause the polymeric aligner to become deformed or damaged when it is removed from the patient's teeth and/or when it is removed from a mold used to manufacture the polymeric aligner.

SUMMARY

An aspect of the disclosure provides a method comprising: determining two or more adjacent teeth in a virtual model, the two or more adjacent teeth comprising a first tooth adjacent to a second tooth in the virtual model; inserting a first virtual filler in the virtual model between the first tooth and the second tooth; selecting a plurality of points in the virtual model, the plurality of points comprising first points on a surface of the first tooth, second points on a surface of the second tooth, third points on a surface of gingiva, and fourth points on the first virtual filler; transforming the plurality of points into a voxel volume comprising a plurality of voxels; performing a smoothing operation on the voxel volume; and subsequent to performing the smoothing operation on the voxel volume, determining, by a processing device, a geometry of an updated virtual filler by transforming a surface of the smoothed voxel volume into a polygonal mesh. In embodiments, selecting the first points on the surface of the first tooth may comprise selecting points on the surface of the first tooth that are within a threshold distance from at least one of the first virtual filler or the surface of the second tooth; and selecting the third points on the surface of the gingiva may comprise selecting points on the surface of the gingiva that are within the a threshold distance of the first virtual filler. In embodiments, in performing the smoothing operation on the voxel volume, the method may comprise: inflating the voxel volume by a first distance field offset to generate an inflated voxel volume; transforming a surface of the inflated voxel volume into an inflated polygonal mesh; transforming the inflated polygonal mesh into an intermediate voxel volume; and deflating the intermediate voxel volume by a second distance field offset to generate the smoothed voxel volume. In embodiments, the second distance field offset is greater than the first distance field offset. In embodiments, in determining the two or more adjacent teeth in the virtual model the method may comprise: determining that the two or more adjacent teeth comprise at least three adjacent teeth in the virtual model that satisfy a crowding criterion indicative of an amount of overlap between the teeth, wherein the at least three adjacent teeth comprise the first tooth, the second tooth, and a third tooth. In embodiments, the method may comprise inserting a second virtual filler in the virtual model between the first tooth and the third tooth; and inserting a third virtual filler in the virtual model between the second tooth and the third tooth, wherein the plurality of points in the virtual model further comprise fifth points on a surface of the third tooth, sixth points on the second virtual filler, and seventh points on the third virtual filler. In embodiments, the first virtual filler in the virtual model inserted between the first tooth and the second tooth is a virtual filler of a predetermined shape. In embodiments, the first virtual filler comprises a first side and a second side, the first side of the first virtual filler located within the first tooth, the second side of the first virtual filler located within the second tooth. In embodiments, the virtual model is a virtual model of a dental arch. In embodiments, the method may further comprise: updating the virtual model to include the updated virtual filler based on the determined geometry. In embodiments, the method further comprises: fabricating a physical mold of the dental arch using the updated virtual model, wherein the physical mold comprises material in an area of the updated virtual filler.

An aspect of the disclosure provides a method comprising: determining three or more adjacent teeth in a virtual model; determining whether the teeth are crowded teeth based on a crowding metric indicative of an amount of overlap between the teeth; responsive to determining that the teeth are crowded teeth, determining a respective portion of each of the teeth on which a virtual filler is to contact; determining a shape that encloses the respective portion of each of the teeth; and determining, by a processing device, a geometry of the virtual filler based on the shape. In embodiments, the virtual model is a virtual model of a dental arch. In embodiments, the method may further comprise: updating the virtual model to include the virtual filler based on the determined geometry. In embodiments, the method may further comprise: fabricating a physical mold of the dental arch using the updated virtual model, wherein the physical mold comprises material in an area of the virtual filler. In embodiments, the method may further comprise: determining a clinical feature on at least one of the teeth; determining whether the clinical feature contacts a first section of any of the respective portions of the teeth; and responsive to determining that the clinical feature contacts the first section, removing the first section from the respective portion of an associated tooth of the teeth. In embodiments, the virtual model comprises a gingival region. In embodiments, the method may further comprise: determining an intersection between the gingival region and the shape; and modifying, based on the intersection, the shape of the virtual filler to determine the geometry of the virtual filler. In embodiments, the method may further comprise: simulating a thermoforming process on the shape that encloses the portion of each of the teeth; and modifying, based on the simulated thermoforming process, the shape to determine the geometry of the virtual filler. In embodiments, the virtual model is a virtual model of a dental arch. In embodiments, wherein determining whether the teeth are crowded teeth, the method may comprise: determining a curvature of the dental arch; determining a plane tangential to a point on the curvature; projecting contours of the teeth on the plane; determining the crowding metric by measuring an amount of overlap of the contours of the teeth; and comparing the crowding metric to a threshold, wherein determining the crowding metric is greater than the threshold indicates the teeth are crowded teeth.

An aspect of the disclosure presents a method comprising: determining a first tooth adjacent to a second tooth in a virtual model; determining a first plane that intersects a front and a rear of the first tooth and a second plane that intersects a front and a rear of the second tooth; generating a first contour within the first tooth and on the first plane and a second contour within the second tooth and on the second plane, wherein the first contour and the second contour are respective sides of a virtual filler; connecting the first contour to the second contour to construct a surface of the virtual filler; and determining, by a processing device, a geometry of the virtual filler based on the first contour, the second contour and the surface. In embodiments, the method may further comprise: determining a location of the virtual filler in the virtual model based on the determining of the first plane and the second plane. In embodiments, the virtual model is a virtual model of a dental arch. In embodiments, the method may further comprise: updating the virtual model to include the virtual filler based on the determined geometry. In embodiments, the method may further comprise: fabricating a physical mold of the dental arch using the updated virtual model, wherein the physical mold comprises material in an area of the virtual filler. In embodiments, wherein determining a first plane that intersects a front and a rear of the first tooth, the method further comprises: generating a three-dimensional (3D) coordinate system with respect to the first tooth, wherein a z-axis of the 3D coordinate system intersects a bottom portion and a top portion of the tooth, and wherein a y-axis of the 3D coordinate system extends in a direction of the second tooth; determining a first point and a second point within the first tooth, wherein the first point and the second point lay along a yz-plane; and generating the first plane containing the first point and the second point, wherein the first plane is perpendicular to the yz-plane. In embodiments, wherein generating a first contour within the first tooth and on the first plane, the method may comprise: determining a third point that is between the first point and the second point and on the yz-plane; determining a plurality of lines from the third point to a surface of the first tooth, wherein each of the plurality of lines extends from the third point to a different point on the surface of the first tooth; determining a plurality of boundary points, wherein each of the boundary points are located on a respective one of the lines a distance from the surface of the tooth; and connecting the boundary points to form the first contour. In embodiments, wherein connecting the first contour to the second contour to construct a surface of the virtual filler, the method may comprise: connecting first boundary points of the first contour to second boundary points of the second contour; smoothing the surface of the virtual filler; and filling the surface of the virtual filler. In embodiments, the method may further comprise: determining a clinical feature on at least one of the first tooth or the second tooth; determining whether the clinical feature contacts the virtual filler; and responsive to determining that the clinical feature contacts the virtual filler, removing a first part of the virtual filler in contact with the clinical feature.

An aspect of the disclosure presents a method comprising: determining two or more adjacent teeth in a virtual model; determining a characteristic of the teeth indicative of a spatial relationship between the teeth; determining that the characteristic satisfies a criterion for a virtual filler; and determining a geometry of the virtual filler based on the spatial relationship between the teeth. In embodiments, to determine that the characteristic satisfies the criterion for a virtual filler, the method may further comprise: determining whether the characteristic satisfies a first criterion or a second criterion. In embodiments, the geometry of the virtual filler is determined based on the respective determined criterion. In embodiments, the method may further comprise: responsive to determining the characteristic satisfies the first criterion, determining a respective portion of each of the teeth on which the virtual filler is to contact; and determining a shape that encloses the respective portion of each of the teeth, wherein the geometry of the virtual filler is based on the shape. In embodiments, the method may further comprise: determining a clinical feature on at least one of the teeth; determining whether the clinical feature contacts a first section of any of the respective portions of the teeth; and responsive to determining that the clinical feature contacts the first section, remove the first section from the respective portion of an associated tooth of the teeth. In embodiments, the method may further comprise: responsive to determining the characteristic satisfies the second criterion, determining a first plane that intersects a front and a rear of a first tooth of the teeth and a second plane that intersects a front and a rear of a second tooth of the teeth; generating a first contour within the first tooth and on the first plane and a second contour within the second tooth and on the second plane, wherein the first contour and the second contour are respective sides of the virtual filler; and connecting the first contour to the second contour to construct a surface of the virtual filler, wherein the geometry of the virtual filler is based on the first contour, the second contour and the surface. In embodiments, to determine the first plane that intersects the front and the rear of the first tooth, the method may further comprise: generating a three-dimensional (3D) coordinate system with respect to the first tooth, wherein a z-axis of the 3D coordinate system intersects a bottom portion and a top portion of the tooth, and wherein a y-axis of the 3D coordinate system extends in a direction of the second tooth; determining a first point and a second point within the first tooth, wherein the first point and the second point lay along a yz-plane; and generating the first plane containing the first point and the second point, wherein the first plane is perpendicular to the yz-plane. In embodiments, to generate the first contour within the first tooth and on the first plane, the method may further comprise: determining a third point that is between the first point and the second point and on the yz-plane; determining a plurality of lines from the third point to a surface of the first tooth, wherein each of the plurality of lines extends from the third point to a different point on the surface of the first tooth; determining a plurality of boundary points, wherein each of the boundary points are located on a respective one of the lines a distance from the surface of the tooth; and connecting the boundary points to form the first contour. In embodiments, the virtual model is a virtual model of a dental arch. In embodiments, the method may further comprise: updating the virtual model to include the virtual filler based on the determined geometry. In embodiments, the method may further comprise: fabricating a physical mold of the dental arch using the updated virtual model, wherein the physical mold comprises material in an area of the virtual filler.

BRIEF DESCRIPTION OF THE DRAWINGS

The present disclosure is illustrated by way of example, and not by way of limitation, in the figures of the accompanying drawings.

FIG. 7 illustrates a virtual model of dental arches with two adjacent teeth with and without virtual fillers, in accordance with embodiments.

DETAILED DESCRIPTION

Figure 1:
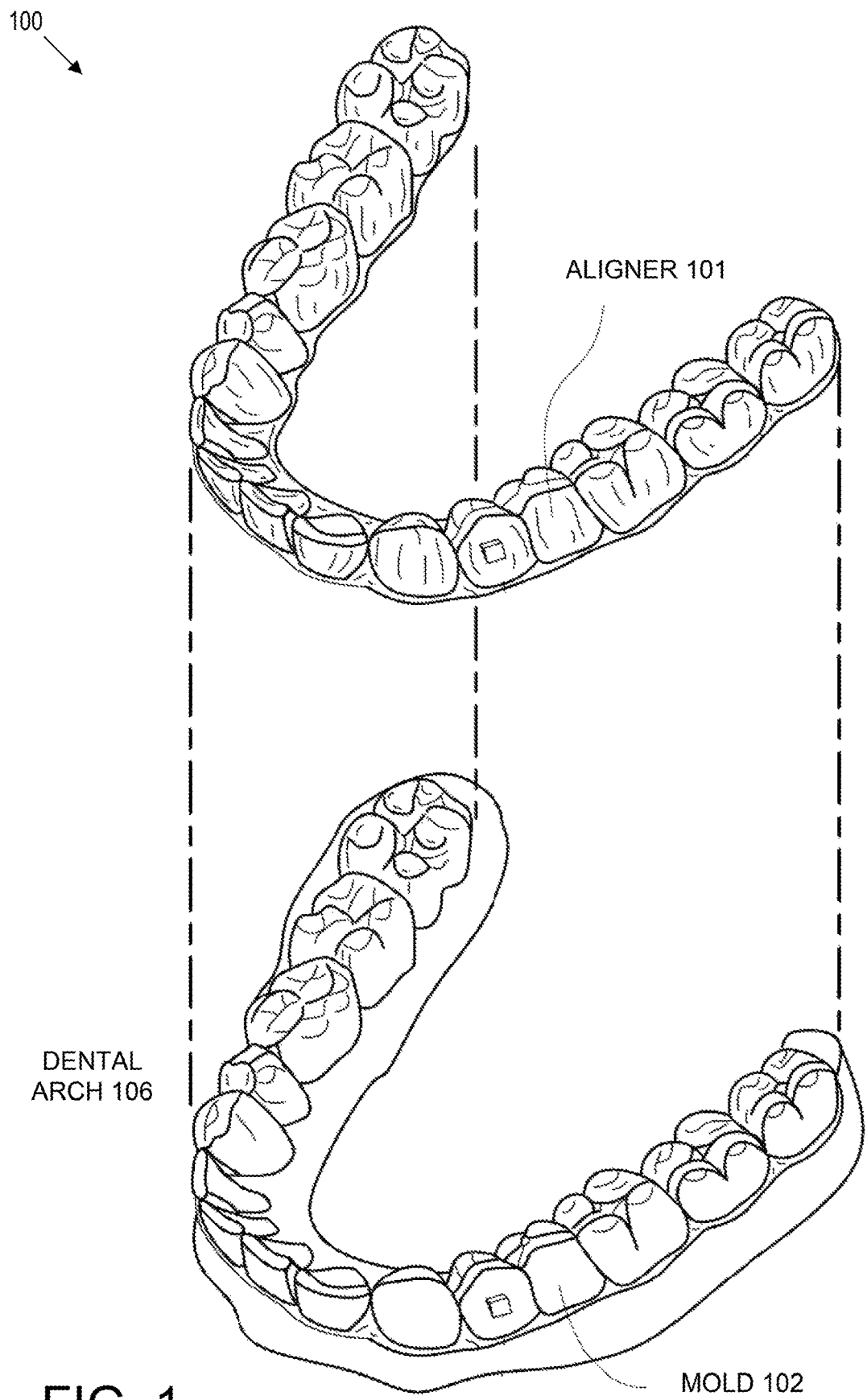
FIG. 1 illustrates an orthodontic aligner and physical mold, in accordance with one embodiment.

Orthodontic aligners (also referred to as "shell aligners," "plastic aligners," "polymeric aligners", or "aligners" herein) described herein, along with related systems and methods, can be employed as part of an orthodontic treatment procedure in order to reposition one or more teeth, maintain a current position of one or more teeth, or suitable combinations thereof. An orthodontic aligner as described herein may be included in a series of orthodontic aligners so as to provide an orthodontic system for positioning teeth. Such an orthodontic system can include a sequence of orthodontic aligners each including a shell having a one or more cavities shaped to receive at least portions of teeth. The series of orthodontic aligners may be successively worn by a patient to move one or more teeth from a first arrangement to a second arrangement.

For each of the series of orthodontic aligners, a virtual model of a dental arch (also referred to as an "arch" herein) may be created. The virtual model may be used to fabricate a physical mold of the dental arch. In turn, the physical mold of the dental arch may be used to fabricate the particular orthodontic aligner in the series. For instance, a thermoforming process may be used to form a plastic orthodontic aligner on the physical mold of the dental arch. In some cases, the geometry of the physical mold may induce quality issues in the orthodontic aligner during or after the thermoforming process. For instance, the geometry of the physical mold may include retentive areas or stress concentration areas that induce quality issues with the orthodontic aligner, such as holes or pinched areas, degradation of material properties (e.g., compression or stretching), or deformation or tearing of the orthodontic aligner during a removal process (e.g., removal of the orthodontic aligner from the physical mold).

Aspects of the present disclosure address the above-mentioned and other challenges by generating virtual fillers for a virtual model of a dental arch, where the virtual fillers reduce the retentive and stress concentration areas of a resultant physical mold. In embodiments, generating a virtual filler includes determining two or more adjacent teeth in a virtual model of a dental arch and determining a characteristic of the teeth indicative of a spatial relationship between the teeth. A determination may be made as to whether the characteristic satisfies a criterion for a virtual filler (e.g., determining that the teeth are crowded teeth or two adjacent teeth). Responsive to the determination, a geometry (e.g., geometric shape and position in the virtual model) of the virtual filler for either crowded teeth or two adjacent teeth may be determined based on the spatial relationship between the teeth.

In some embodiments, generating a virtual filler includes determining two or more adjacent teeth in a virtual model. The two or more adjacent teeth include a first tooth adjacent to a second tooth in the virtual model. A first virtual filler is inserted in the virtual model between the first tooth and the second tooth. Points are selected in the virtual model. The selected points include first points on a surface of the first tooth, second points on a surface of the second tooth, third points on a surface of gingiva, and fourth points on the first virtual filler. The points are transformed into a voxel volume. A smoothing operation is performed on the voxel volume. Subsequent to performing the smoothing operation on the voxel volume, a geometry of an updated virtual filler is determined by transforming a surface of the smoothed voxel volume into a polygonal mesh.

A virtual filler may refer to a digital feature of or added to a virtual model (such as a virtual model of a dental arch) that presents an additional object between two or more adjacent teeth. In embodiments, the virtual filler of the virtual model changes the geometry of a respective physical mold and reduces the probability of fabrication issues.

Generating virtual fillers for virtual models, as disclosed herein, is advantageous at least because the virtual filler of the virtual model changes the geometry of a respective physical mold to reduce retentive and stress concentration areas, which reduces the probability of quality issues during and after the fabrication of orthodontic aligners. Further, aspects of the present disclosure result in reduction of storage resources and computational (processing) resources at least because the virtual fillers may be used and re-used in the creation of multiple physical molds (e.g., data stored and processing resources are reduced because the number of virtual fillers is also reduced) and the virtual fillers help reduce the number of fabrication processes (e.g., a particular orthodontic aligner may be fabricated once as a result of the reduction of quality issues). In addition, aspects of the present disclosure result in improvements in the fabrication of orthodontic aligners.

Embodiments are discussed herein with reference to orthodontic aligners. The orthodontic aligners described herein are generally plastic shells that are thermoformed over a physical mold that has been manufactured using a virtual three-dimensional (3D) model of a dental arch. It should be noted that embodiments described herein with reference to orthodontic aligners also apply to other plastic shells worn over a patients teeth, such as sleep apnea appliances, appliances used for surgical stabilization (e.g., for use during and/or after surgery that corrects type I, type II and/or type III malocclusions), orthodontic retainers, orthodontic splints, and so on. Accordingly, any discussion of orthodontic aligners also applies to other such plastic shells that are worn over a patient's teeth.

FIG. 1 illustrates an orthodontic aligner and physical mold, in accordance with one embodiment. Diagram 100 illustrates an example of a tooth repositioning appliance, such as orthodontic aligner 101 that can be worn by a patient in order to achieve an incremental repositioning of individual teeth in the jaw. The orthodontic aligner 101 can include a shell (e.g., a translucent polymeric shell) having teeth-receiving cavities that receive and resiliently reposition the teeth. The orthodontic aligner 101 or portion(s) thereof may be indirectly fabricated using a physical model or physical mold 102 of the teeth. In embodiments, the physical mold 102 may be a mold of a patient's dental arch 106. A dental arch may refer to a crescent arrangement of teeth. Each jaw may include two dental arches that constitute a dentition. In embodiments, orthodontic aligner 101 can be formed using a physical mold 102 and a sheet of suitable layers of polymeric material. An orthodontic aligner 101 can fit over all teeth present in an upper or lower jaw (e.g., upper dental arch or lower dental arch), or less than all of the teeth. The orthodontic aligner 101 can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the orthodontic aligner 101 can be a generic aligner configured to receive the teeth, but not necessarily shaped to match the topography of the patient's teeth.

In some embodiments, only certain teeth received by an orthodontic aligner 101 will be repositioned by the orthodontic aligner 101 while other teeth can provide a base or anchor region for holding the appliance in place as the orthodontic aligner 101 applies force against the tooth or teeth targeted for repositioning. In some cases, many or most, and even all, of the teeth will be repositioned at some point during treatment. Teeth that are moved can also serve as a base or anchor for holding the orthodontic aligner 101 as the aligner is worn by the patient. Typically, no wires or other means will be provided for holding an orthodontic aligner 101 in place over the teeth. In some cases, however, it may be desirable to provide individual attachments or other anchoring elements (not shown) on teeth with corresponding receptacles or apertures (not shown) in the orthodontic aligner 101 so that the aligner can apply a selected force on the tooth.

Figure 20:
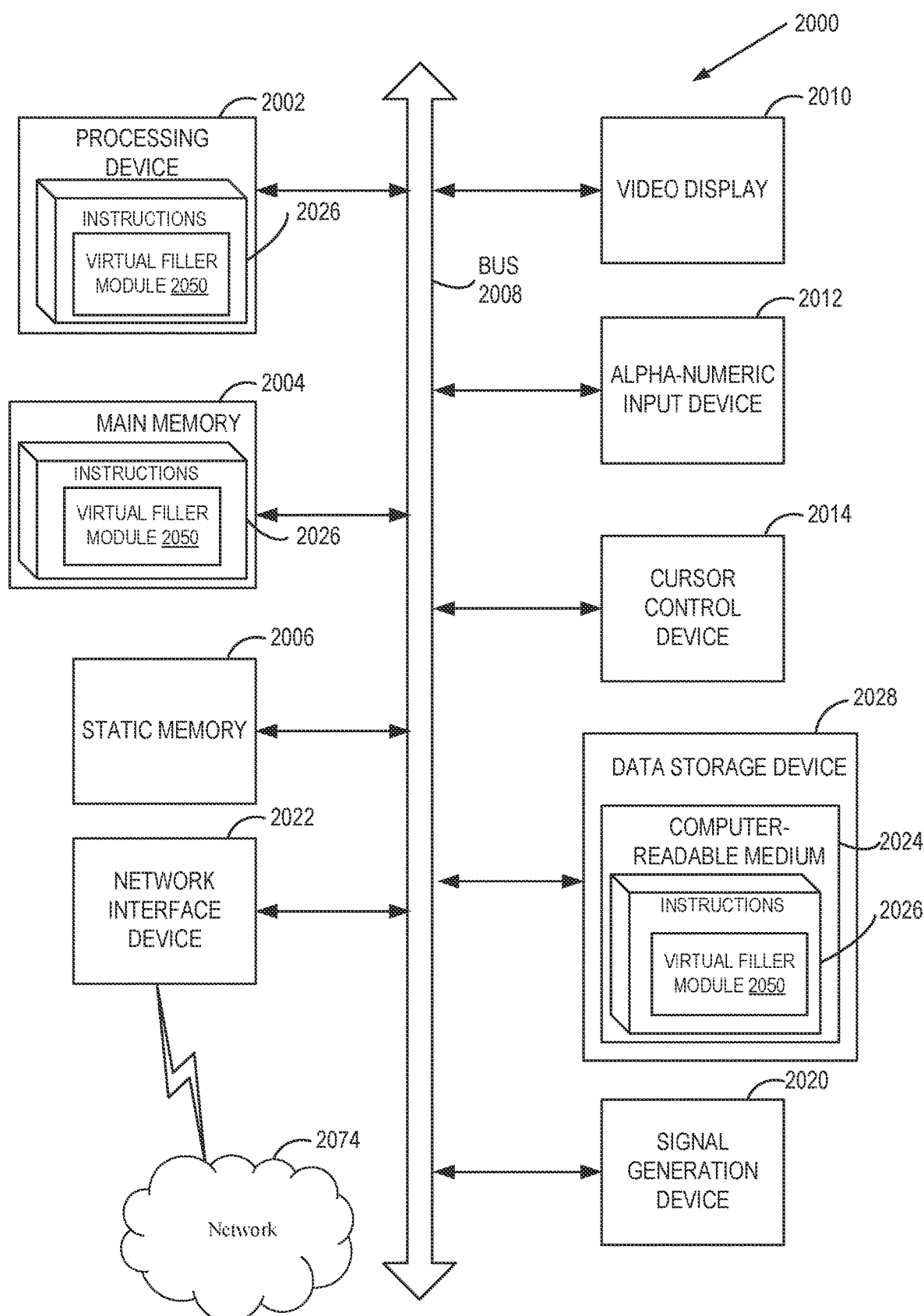
FIG. 20 illustrates a block diagram of an example computing device, in accordance with embodiments of the present disclosure.

In some embodiments, orthodontic aligner 101 may be fabricated by one or more operations. For example, one or more operations may be performed by a processing device executing a computer aided drafting (CAD) program or virtual filler module 2050 as illustrated in FIG. 20. It may be noted that operations described in the disclosure herein may be performed by a virtual filler module 2050, unless otherwise described. The aligner development and fabrication process is described in the following description. In embodiments, a virtual patient is created. A virtual patient is a digital file, database entry, or data structure that represents a patient. The virtual patient may include patient data, photographs, a virtual model (e.g., virtual three-dimensional (3D) model of a patient's dental arch), x-ray images of a patient's dentition, and so on. The virtual patient may be created based on input data in the form of intraoral scan data, a PVS (polyvinyl siloxane) impression or the like, (e.g., a PVS file or a 3DM file), a sterolithography (STL) file, an align design file (ADF), digital photographs (e.g., JPG files, BMP files, PNG files, and so on), stereo photos, videos (e.g., MPEG files), x-ray images (e.g., cone beam computerized tomography CBCT scan) and/or other input data. If a virtual 3D model of the patient's upper and lower dental arches are not yet included in the virtual patient, then such virtual 3D models may be generated from the input data.

In an example, an intraoral scan of the patient's dental arches may be performed to generate the virtual 3D model of the patient's upper and lower dental arches. For example, a full scan of the mandibular and/or maxillary arches of a patient may be performed to generate virtual 3D models thereof. The intraoral scan may be performed by creating multiple overlapping intraoral images from different scanning stations and then stitching together the intraoral images to provide a composite virtual 3D model. In other applications, virtual 3D models may also be generated based on scans of an object to be modeled or based on use of computer aided drafting techniques (e.g., to design the virtual 3D mold). Alternatively, an initial negative mold may be generated from an actual object to be modeled. The negative mold may then be scanned to determine a shape of a positive mold that will be produced.

In embodiments, an initial dental orientation is defined (e.g., before the start or treatment with orthodontic aligner 101). The initial dental orientation includes an initial position of the upper and lower jaw, including an initial relationship in position and orientation between the upper and lower jaw. The initial dental orientation is the initial position, orientation, and relationship for and between the upper and lower dental arches before treatment with orthodontic aligner 101. The initial dental orientation defines the starting point for orthodontic treatment and the initial shapes of the upper and lower dental arches, and the fixed relationship between the upper and lower dental arch, during a post-operative fixation period.

In embodiments, once the initial dental orientation target is defined, a final treatment goal is defined. The final treatment goal is the target dental positions and orientations for the patient's teeth post treatment with orthodontic aligner 101. In embodiments, a sequence of treatment stages are determined to reposition the teeth from the starting dentition defined from the initial dental orientation to the final treatment goal. This may include determining a number of treatment stages that should be used to cause the teeth to progress from initial positions and orientations to the target final positions and orientations. Each treatment stage may move the patient's teeth slightly toward the final treatment goal. The shape of the final virtual 3D model and each intermediate virtual 3D model may be determined by computing the progression of tooth movement throughout orthodontic treatment from initial tooth placement and orientation to final corrected tooth placement and orientation. For each treatment stage, a separate virtual 3D model of the patient's dental arches at that treatment stage may be generated. The shape of each virtual 3D model will be different. The original virtual 3D model, the final virtual 3D model and each intermediate virtual 3D model is unique and customized to the patient. A treatment plan may be generated that includes the surgical target, final treatment goal and each of the treatment stages (including the virtual 3D models of the arches at each treatment stage).

In embodiments, multiple different virtual 3D models may be generated for a single patient. A first pair of virtual 3D models may be a unique pair of models of a patient's dental arches and/or teeth as they will exist after the surgery, and a final virtual 3D model may be a model of the patient's dental arch and/or teeth after both surgery and orthodontic correction of one or more teeth and/or a jaw. Multiple intermediate virtual 3D models may be modeled, each of which may be incrementally different from previous virtual 3D models.

In embodiments, orthodontic aligners 101 are fabricated based on the virtual 3D models of the dental arches for one or more treatment stages. In one embodiment, rapid prototyping (e.g., stereo lithography) is performed to form physical molds 102 from the virtual 3D models for one or more treatment stages. One example of a rapid prototyping manufacturing machine is a 3D printer. 3D Printing includes any layer-based additive manufacturing processes. 3D printing may be achieved using an additive process, where successive layers of material are formed in proscribed shapes. 3D printing may be performed using extrusion deposition, granular materials binding, lamination, photopolymerization, continuous liquid interface production (CLIP), or other techniques. 3D printing may also be achieved using a subtractive process, such as milling.

In one embodiment, stereolithography (SLA), also known as optical fabrication solid imaging, is used to fabricate an SLA mold. In SLA, the physical mold 102 is fabricated by successively printing thin layers of a photo-curable material (e.g., a polymeric resin) on top of one another. A platform rests in a bath of a liquid photopolymer or resin just below a surface of the bath. A light source (e.g., an ultraviolet laser) traces a pattern over the platform, curing the photopolymer where the light source is directed, to form a first layer of the physical mold 102. The platform is lowered incrementally, and the light source traces a new pattern over the platform to form another layer of the physical mold 102 at each increment. This process repeats until the physical mold 102 is completely fabricated. Once all of the layers of the physical mold 102 are formed, the mold may be cleaned and cured.

Materials such as a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate, a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, a thermoplastic polyamide elastomer, or combinations thereof, may be used to directly form the physical mold 102. The materials used for fabrication of the physical mold 102 can be provided in an uncured form (e.g., as a liquid, resin, powder, etc.) and can be cured (e.g., by photopolymerization, light curing, gas curing, laser curing, crosslinking, etc.). The properties of the material before curing may differ from the properties of the material after curing.

In embodiments, orthodontic aligners 101 may be formed from each physical mold 102 to provide forces to move the patient's teeth. The shape of each orthodontic aligner 101 is unique and customized for a particular patient and a particular treatment stage. In an example, the orthodontic aligner 101 can be pressure formed or thermoformed over the physical molds 102. In one embodiment, a sheet of material is pressure formed or thermoformed over the physical mold 102. The sheet may be, for example, a sheet of plastic (e.g., an elastic thermoplastic, a sheet of polymeric material, etc.). To thermoform the orthodontic aligner 101 over the physical mold 102, the sheet of material may be heated to a temperature at which the sheet becomes pliable. Pressure may concurrently be applied to the sheet to form the now pliable sheet around the physical mold 102 with the features that will imprint the markings and/or elements in the orthodontic aligner 101. Once the sheet cools, it will have a shape that conforms to the physical mold 102. In one embodiment, a release agent (e.g., a non-stick material) is applied to the physical mold 102 before forming the orthodontic aligner 101. This may facilitate later removal of the physical mold 102 from the orthodontic aligner 101. After thermoforming, the orthodontic aligner 101 may be trimmed at a cut line that is near to a gingival line of the patient.

In embodiments, each physical mold 102 may be used to fabricate an orthodontic aligner 101 that will apply forces to the patient's teeth at a particular stage of the orthodontic treatment. The orthodontic aligners 101 each have teeth-receiving cavities that receive and resiliently reposition the teeth in accordance with a particular treatment stage. The orthodontic aligners 101 may additionally have stabilization features that will maintain target positions and orientation of the upper and lower jaw during the post-operative fixation period.

One of more of the virtual 3D models of the upper and/or lower dental arches may include features (e.g., undercuts, sharp corners, crowded areas, etc.) that will ultimately cause manufacturing difficulties. Such features will be transferred to the physical molds generated from the virtual 3D models. After thermoforming is performed, these features may cause the orthodontic aligner to be retained on the mold, and may make removal of the orthodontic aligner from the mold difficult and/or error prone. Moreover, these features may cause the orthodontic aligners to be too thin in regions, to be damaged during removal of the orthodontic aligners from the physical molds, and so on. Virtual fillers may therefore be added to the virtual 3D models to remove problematic features and/or to mitigate the impact of such problematic features, as set forth herein below. Multiple different techniques for generating virtual fillers are provided herein. A first technique for generating virtual fillers is used for crowded teeth, and a second technique for generating virtual fillers is used for pairs of adjacent teeth. Another technique that is described may be used both for generating virtual fillers used for crowded teeth as well as for generating virtual fillers used for adjacent teeth (e.g., may be used for virtual filler between two or more teeth).

Figure 2:
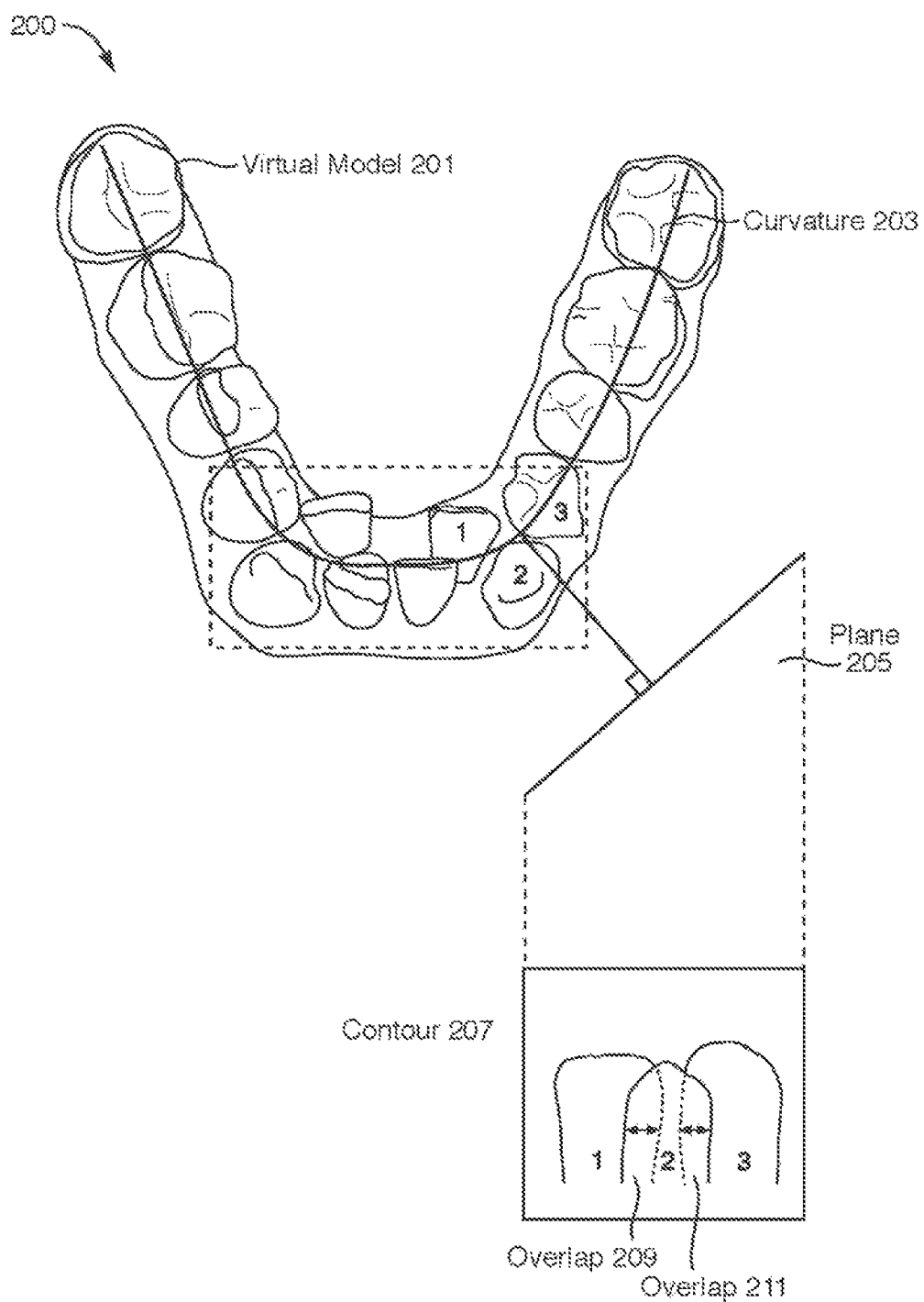
FIG. 2 illustrates a virtual model of a dental arch with crowded teeth, in accordance with embodiments.

FIG. 2 illustrates a virtual model of a dental arch with crowded teeth, in accordance with embodiments. Diagram 200 shows a virtual model 201 of a dental arch having crowded teeth. In embodiments, crowded teeth may refer to three or more adjacent teeth (herein after referred to as "teeth" unless otherwise described) having a threshold amount of overlap between the teeth (e.g., teeth 1, 2, and 3 are crowded together). The amount of overlap of the teeth may be a characteristic of crowded teeth (e.g., spatial relationship between the teeth). It may be noted that three or more adjacent teeth may also be considered a characteristic of crowded teeth. In some embodiments, the amount of overlap between the teeth may be compared to a criterion, such as a threshold (e.g., distance in millimeters (mm)), to determine whether the teeth are crowded teeth.

In some embodiments, determining whether the teeth are crowded teeth includes determining a curvature 203 of the dental arch. In embodiments, the curvature 203 may be a line that estimates or approximates the curvature of the dental arch. A plane 205 that is tangential to a point on the curvature 203 may be determined. For example, a point at approximately the center of tooth 2 may be located. A line orthogonal to the center of tooth 2 may be generated. Plane 205 may then be generated, where plane 205 is orthogonal to the line. In embodiments, a similar operation may be performed on each tooth of the virtual model 201 of the dental arch. For example, a plane tangential to a point on each tooth may be generated.

In embodiments, the two-dimensional contours (e.g., outline) of adjacent teeth may be projected on the plane 205. For the sake of illustration, rather than limitation, the contours 207 of tooth 1, tooth 2, and tooth 3 are shown projected on plane 205. A crowding metric indicative of the amount of overlap between the teeth may be determined. For example, a crowding metric may be determined by measuring the amount of overlap of the contours for each pair of adjacent teeth of the three or more adjacent teeth 1, 2, 3. In some embodiments, the amount of overlap of the contours may be the maximum distance between the intersections of contours for a pair of teeth. For example, the overlap 209 of tooth 1 and tooth 2 may be 2 mm and the overlap 211 of tooth 2 and tooth 3 may be 1 mm. In some embodiments, the crowding metric may be the sum of the overlap between the contours 207. For example, for teeth 1-3 the crowding metric may be the sum of overlap 209 and overlap 211 (e.g., 3 mm of overlap). The crowding metric (e.g., 3 mm of overlap) may be compared to a threshold (e.g. 2.5 mm). Responsive to determining that the crowding metric is below the threshold, the teeth may be considered uncrowded teeth. Responsive to determining that the crowding metric is equal to or greater than the threshold, the teeth may be considered crowded teeth. In embodiments, the threshold may be pre-determined by a developer or adjusted on a per patient basis, for example. In embodiments, each tooth may be examined in similar manner as described to determine if the tooth is part of a crowded teeth structure. It may be noted that tooth 1, 2, and 3 as described with respect to FIGS. 2-6B refer to the respective teeth of virtual model 201 of the dental arch of FIG. 2.

Once a determination is made that a dental arch includes crowded teeth, one or more operations may be performed to generate a virtual filler (or multiple virtual fillers) that will contact one or more of the crowded teeth. A first set of operations may be performed to determine portions of one or more teeth that will contact a virtual filler. Portions of a tooth an area (e.g., surface area or internal area) of a tooth that will contact a virtual filler or that will be include in a shape that defines the geometry of the virtual filler.

Figure 3:
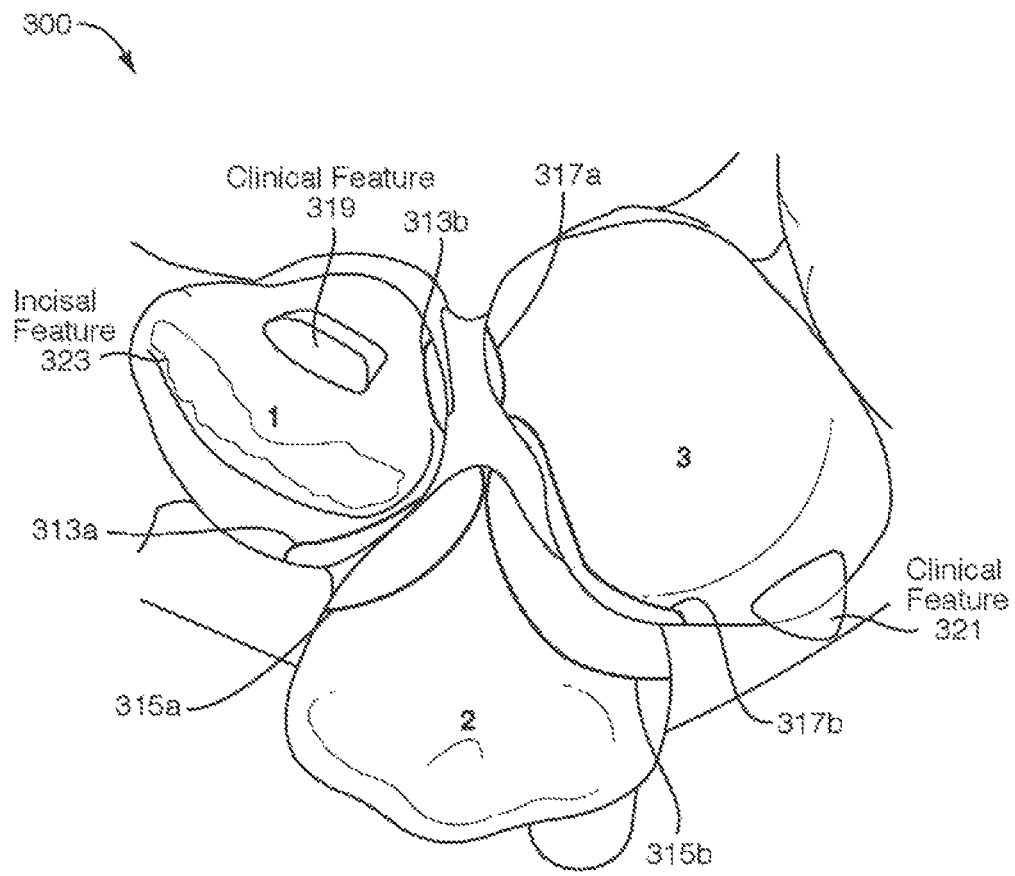
FIG. 3 illustrates portions of crowded teeth on which a virtual filler contacts, in accordance with embodiments.

FIG. 3 illustrates portions of crowded teeth on which a virtual filler contacts, in accordance with embodiments. Diagram 300 shows a magnified view of the crowded teeth (tooth 1, tooth 2, and tooth 3) identified in FIG. 2. In embodiments, responsive to determining that the teeth (i.e., teeth 1-3) are crowded teeth, a respective portion of each of the teeth on which the virtual filler is to contact is determined. For example, tooth 1 includes portion 313A and portion 313B (collectively referred to as portion 313). Tooth 2 includes portion 315A and portion 315B (collectively referred to as portion 315). Tooth 3 includes portion 317A and portion 317B (collectively referred to as portion 317).

In some embodiments, the portions of the teeth that are to contact a virtual filler are determined by aggregating all the points (i.e., countably additive points) that are less than or equal to a threshold distance from an adjacent tooth. For instance, portion 315A of tooth 2 includes all the points that are less than or equal to a threshold distance from tooth 1. Similarly, portion 315B of tooth 2 includes all the points that are less than or equal to a threshold distance from tooth 3. In some embodiments, the portions may be determined by calculating distances between all points for a pair of teeth (e.g., distance between all points of tooth 1 to all points of tooth 2). Points that are below or equal to the threshold are included as part of the portion for a respective tooth, and points greater than the threshold are discarded.

In some embodiments, the portions of the teeth may be adjusted to account for clinical features on the teeth. A clinical feature may be a foreign object located on or attached to a tooth. For example, a clinical feature may include a filling, a bridge, a bracket (of braces), and so forth. Diagram 300 shows clinical feature 319 on tooth 1 and clinical feature 321 on tooth 3. In embodiments, a clinical feature may be detected on at least one of the teeth. For example, clinical feature 319 may be detected on tooth 1. A determination may be made whether the clinical feature contacts any section of any portions of the teeth. For example, clinical feature 319 may be examined to determine whether clinical feature 319 contacts any section of any portions 313, 315, or 317. Responsive to determining that a clinical feature contacts a section of a portion of a tooth, the section of the respective portion may be removed from consideration. For example, if clinical feature 319 were determined to overlap a section of portion 313B (which is not the case in diagram 300), portion 313B would be reduced in size so that there is no overlap between clinical feature 319 and portion 313B. Responsive to determining that a clinical feature does not contact a section of a portion of a tooth, the portion of the tooth is not adjusted.

In some embodiments, the portions of the teeth may be adjusted to account for incisal areas (also referred to as "occlusal areas" herein) of the teeth. An incisal area may be an area of the tooth that is used for eating or an area that contacts with an opposing tooth in the opposing dental arch. In embodiments, an incisal area of each tooth (tooth 1-3) may be determined. For example, an outline of incisal area 323 of tooth 1 is shown in diagram 300. A determination is made whether the incisal area contacts a section of any respective portions of the teeth. For example, virtual filler module 2050 may determine whether incisal area 323 contacts any section of portion 313A or 313B of tooth 1. Responsive to determining that the incisal area contacts a section of any portions of a tooth, the section is removed from the respective portion of the tooth. For example, if incisal area 323 were determined to overlap a section of portion 313A or portion 313B (which is not the case in diagram 300), portion 313 would be reduced in size so that there is no overlap between incisal area 323 and the respective section of portion 313. Responsive to determining that an incisal area does not contact a section of a portion of a tooth, the portion of the tooth is not adjusted.

Figure 4:
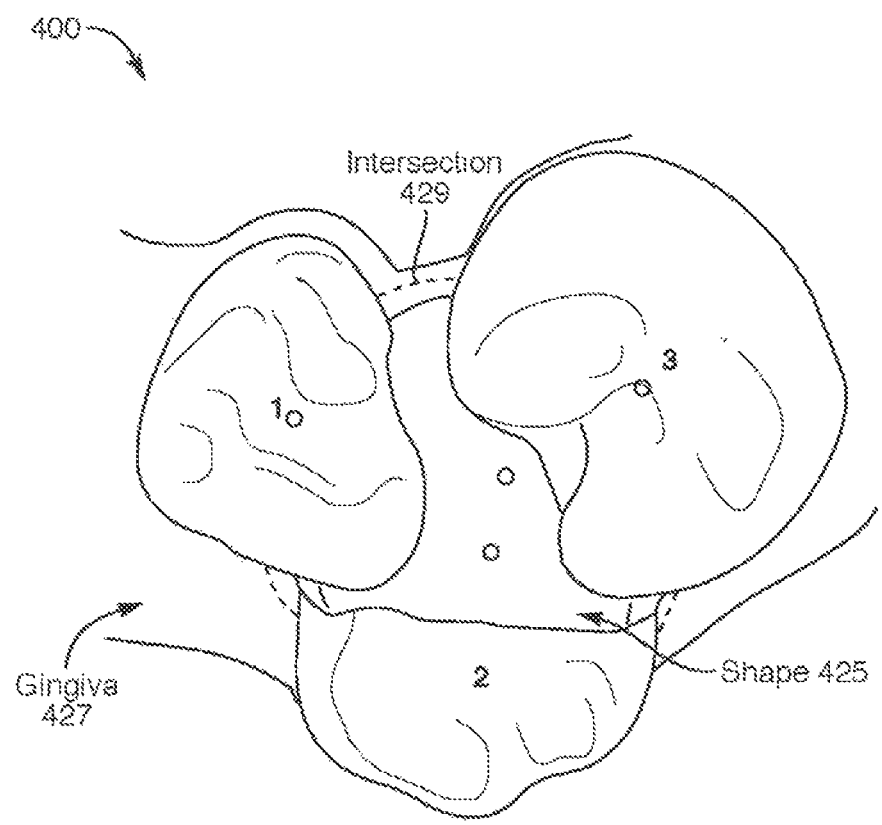
FIG. 4 illustrates a shape that encloses respective portions of the crowded teeth, in accordance with embodiments.

After the portions of teeth that will contact a virtual filler are determined, a shape of the virtual filler may be determined. FIG. 4 illustrates a shape that encloses respective portions of the crowded teeth 1, 2, 3, in accordance with embodiments. Diagram 400 shows shape 425 that encloses the respective portion (i.e., portion 313, 315, and 317 of FIG. 3) of each of the teeth 1, 2, and 3. In embodiments, shape 425 may be a convex hull. A convex hull may be a shape (e.g., smallest convex polygon) that includes a set of X points in an affine space that contains the set of X points.

In embodiments, shape 425 may be adjusted in view of gingiva 427 near the teeth. Gingiva (also referred to as "gums" or "gingival region" herein) may be the tissue that lies over the mandible or maxilla and surrounds the base of the teeth. In an embodiment, gingiva 427 may be projected under and slightly around the shape 425. The virtual filler module 2050 may determine the intersection 429 of the gingiva 427 and the shape 425. For instance, the intersection 429 may include the gingiva 427 directly under the shape 425. In some embodiments, the intersection 429 may also include some amount of gingiva 427 around the shape 425 (e.g., some distance X from directly underneath the shape 425). The points (i.e., countably additive points) of the intersection 429 may be added to the set of points for the portions 313, 315, and 317. Shape 425 may be modified to include the set of points for the portions 313, 315, and 317 and the points of the intersection 429 between the gingiva 427 and the shape 425.

In some embodiments, shape 425 may be adjusted to account for a simulated physical process. For example, the shape 425 may be adjusted to account for the deformation of an orthodontic aligner that undergoes a thermoforming process as part of the fabrication process. In some embodiments, a thermoforming process may be simulated on the shape 425 that encloses the portion of each of the teeth. The shape 425 may be modified based on the simulated thermoforming process. In some embodiments, the thermoforming process may be simulated by simulating a pressure on the outer-facing surface of the shape 425 and a vacuum on the inner-facing surface of the shape 425. The shape 425 may deform (and often shrink) responsive the simulation of the thermoforming process, and the shape 425 may be adjusted to conform to the simulated deformation. In some embodiments, the shape 425 may be adjusted to account for a simulated physical process after shape 425 is adjusted in view of gingiva 427 near the teeth. In one embodiment, the simulated process applies elastic forces between points on a surface of the shape. These elastic forces may reduce the distance between the points on the surface and thus cause the shape to effectively shrink by some amount. In one embodiment, the points on the surface that contact any of the teeth 1, 2, 3 are fixed so that no forces are applied to those points.

Figure 5:
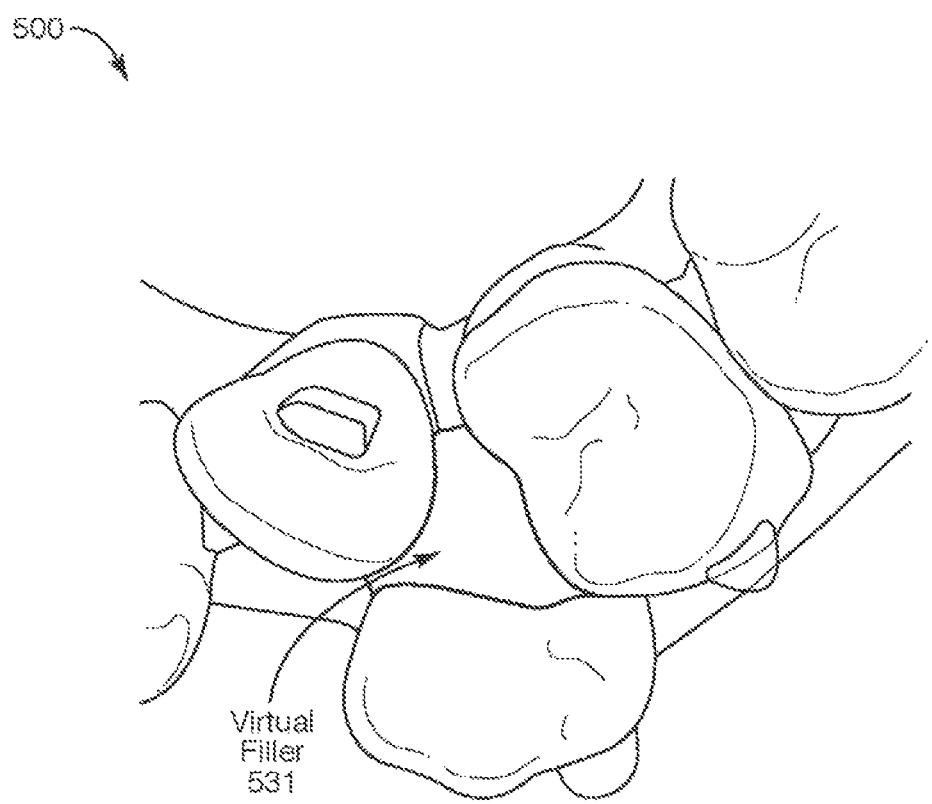
FIG. 5 illustrates a virtual filler for crowded teeth, in accordance with embodiments.

FIG. 5 illustrates a virtual filler for crowded teeth, in accordance with embodiments. Diagram 500 shows a virtual filler 531 for the crowded teeth (tooth 1, 2, and 3) after the above described operations have been performed. In embodiments, the geometry of the virtual filler 531 may be based on the shape 425. In some embodiments, shape 425 may be the geometry of the virtual filler 531. In other embodiments, the geometry of the virtual filler 531 may be determined by smoothing the shape 425 (e.g., the shape may be smoothed to reduce the number of edges or vertices). In embodiments, the virtual filler 531 is part of a virtual model 201 of a dental arch. The virtual model 201 may be updated to include the virtual filler 531 based on the determined geometry. The geometry may include the 3D shape of the virtual filler 531 as well as the location of the virtual filler with respect to the teeth in the virtual model. It may be noted that the virtual model 201 may be used to determine any number of sets of crowded teeth. For each set of crowded teeth, a virtual filler may be generated as described herein. Each virtual filler for the different sets of crowded teeth may be included in the virtual model 201 of the dental arch. In embodiments, a physical mold of the dental arch may be fabricated based on the virtual model 201 that includes the one or more virtual fillers for crowded teeth.

Figure 6A:
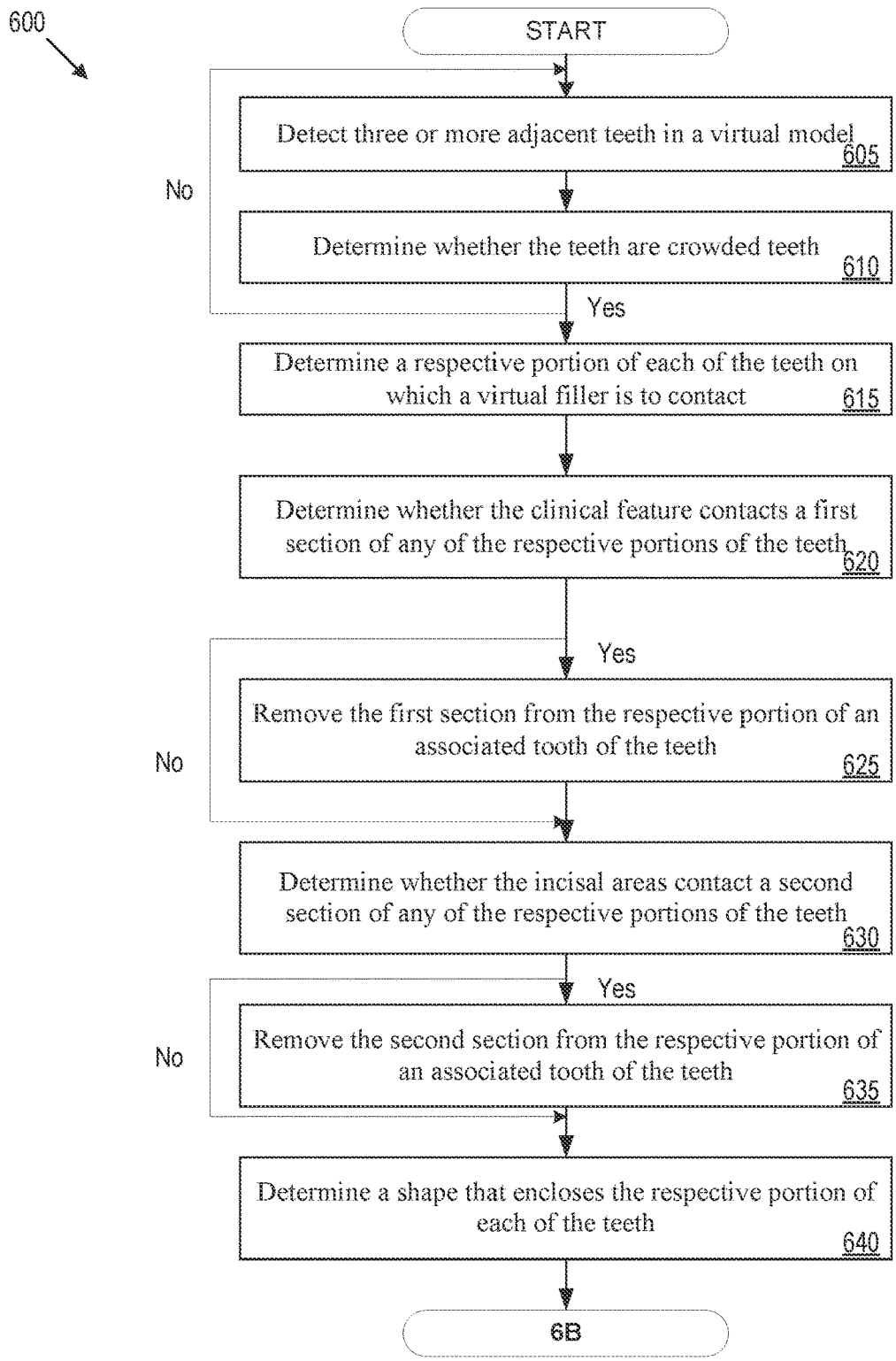
FIGS. 6A-6B illustrates a flow diagram for a method of creating a virtual filler for crowded teeth, in accordance with one embodiment.
Figure 6B:
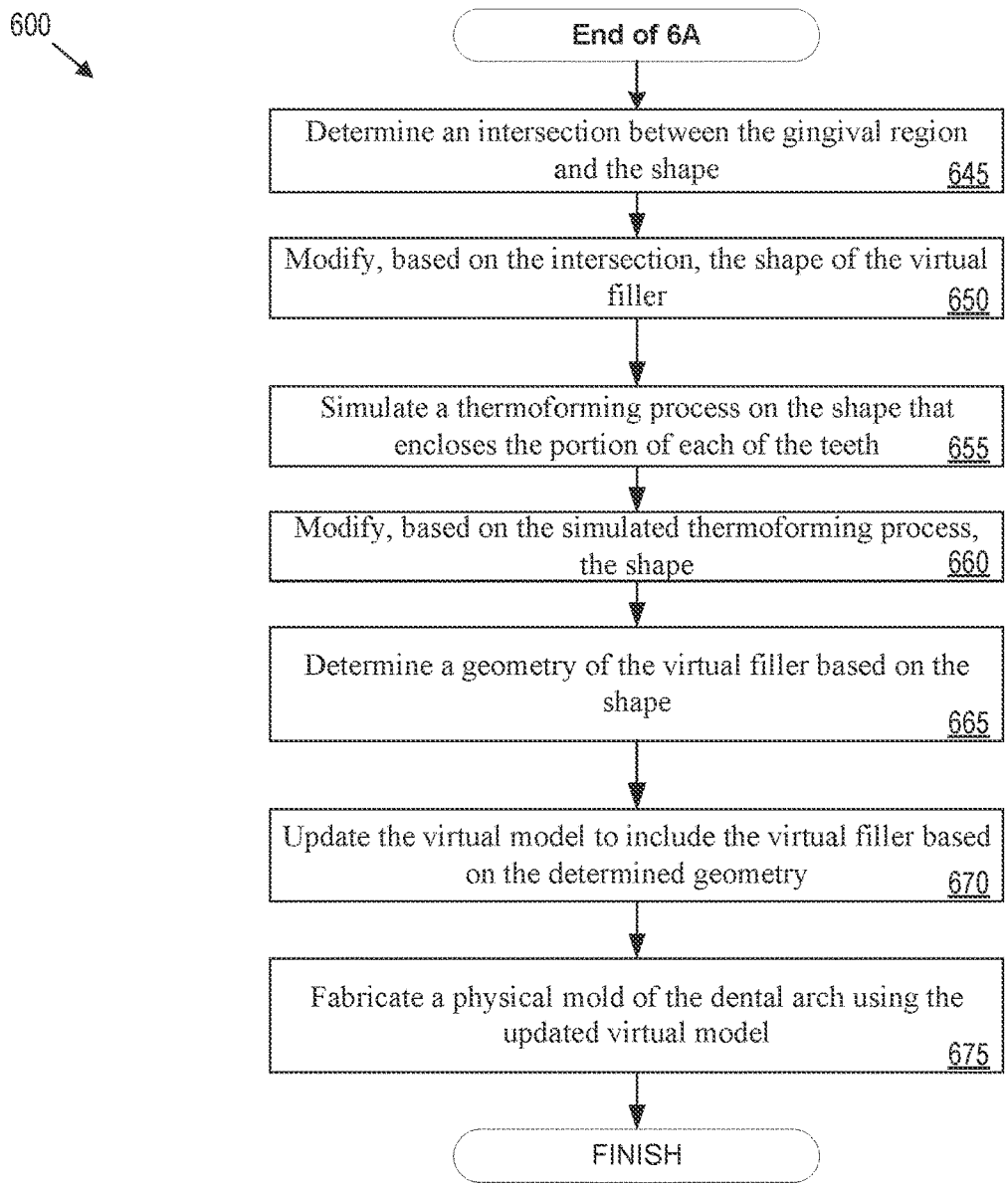

FIGS. 6A-6B illustrate a flow diagram for a method 600 of creating a virtual filler for crowded teeth, in accordance with one embodiment. One or more operations of method 600 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 600 may be performed by a processing device executing a computer aided drafting (CAD) program or module such as a virtual filler module 2050. Elements of the previous figures may be used to help illustrate method 600. It may be appreciated that the in some implementations, method 600 may include the same, different, fewer, or greater operations performed in any order.

In embodiments, processing logic in performing method 600 begins at block 605 by detecting three or more adjacent teeth in a virtual model. For example, processing logic may scan the virtual model 201 to detect a group of three teeth that are directly adjacent to one another. At block 610, processing logic determines whether the teeth are crowded teeth based on a crowding metric indicative of an amount of overlap between the teeth (e.g., as described with reference to FIG. 2). Responsive to determining that the teeth are not crowded teeth (e.g., comparing characteristics of the teeth to a criterion), processing logic may return to block 605 to determine whether other teeth of a dental arch are crowded teeth. Responsive to determining that the teeth are crowded teeth, processing logic moves to block 615. At block 615, processing logic determines a respective portion of each of the teeth on which a virtual filler is to contact. The portions of the teeth on which the virtual filler is to contact are determined as described with reference to FIG. 3.

At block 620, processing logic determines whether a clinical feature contacts a first section of any of the respective portions of the teeth. It may be noted that processing logic may also detect a clinical features on at least one of the teeth prior to the determining of block 620. For example, a feature of a virtual model 201 may be labeled as a clinical feature and processing logic may use location information to locate the clinical feature on the virtual model. Responsive to determining that a clinical feature does not contact a first section of any of the respective portions of the teeth, processing logic moves to block 630. Responsive to determining that the clinical feature contacts a first section of any of the respective portions of the teeth, processing logic moves to block 625. At block 625, processing logic removes the first section from the respective portion of an associated tooth of the teeth.

At block 630, processing logic determines whether the incisal areas contact a second section of any of the respective portions of the teeth. It may be noted that processing logic may also determine the incisal areas of the teeth prior to the determining of block 630. For example, a surface of tooth of a virtual model 201 may be labeled as an incisal area and processing logic may use location information to locate the incisal area on the specific tooth of virtual model. Responsive to determining that an incisal area does not contact a second section of any of the respective portions of the teeth, processing logic moves to block 640. Responsive to determining that an incisal area contacts a second section of any of the respective portions of the teeth, processing logic moves to block 635. At block 635, processing logic removes the second section from the respective portion of an associated tooth of the teeth. At block 640, processing logic determines a shape that encloses the respective portion of each of the teeth (after the regions that contacted clinical features and/or incisal areas have been removed). The shape represents an initial shape of the virtual filler.

Method 600 moves from block 640 of FIG. 6A to block 645 of FIG. 6B. At block 645, processing logic determines an intersection between the gingival region and the shape of the virtual filler. At block 650, processing logic modifies, based on the intersection, the shape of the virtual filler. The shape of the virtual filler is adjusted as described above with reference to FIG. 4. In one embodiment, at block 655, processing logic simulates a thermoforming process on the shape that encloses the portion of each of the teeth. At block 660, processing logic modifies the shape based on the simulated thermoforming process.

At block 665, processing logic determines a geometry of the virtual filler based on the shape. At block 670, processing logic updates the virtual model to include the virtual filler based on the determined geometry. Alternatively, the virtual model may be updated at one or more of blocks 640-660 to include the virtual model. In such an embodiment, blocks 665 and/or 670 may be omitted. At block 675, processing logic fabricates a physical mold of the dental arch using the updated virtual model. This may include outputting a file that contains instructions for fabricating the dental arch with the virtual filler to a rapid prototyping machine. The rapid prototyping machine (e.g., an SLA machine) may then manufacture the physical model from the file. The physical mold includes material in an area of the virtual filler.

A second technique for generating virtual fillers may be used for virtual fillers between pairs of adjacent teeth that are not crowded.

FIG. 7 illustrates a virtual model of dental arches with two adjacent teeth with and without virtual fillers, in accordance with embodiments. Diagram 700 shows a virtual model 701A of a dental arch without virtual fillers and a virtual model 701B of a dental arch with virtual fillers, such as virtual filler 703. In embodiments, two adjacent teeth may refer to any two teeth that are directly adjacent to one another (i.e., no intervening teeth). The distance between the two adjacent teeth (also referred to as "adjacent teeth" herein, unless otherwise described) may be a characteristic of the adjacent teeth. Adjacent teeth that are directly adjacent teeth may be another characteristic. In some embodiments, another characteristic of adjacent teeth may be that the two teeth are not part of a crowded tooth structure, as described herein. In some embodiments, the distance between the adjacent teeth may be compared to a criterion, such as a threshold (e.g., distance in millimeters (mm)), to determine whether the teeth are adjacent teeth. For example, two teeth that are directly adjacent and have a distance between the two teeth of less than X millimeters may be considered adjacent teeth. It may be noted that all the teeth of virtual model 701A may be checked to determine whether the pairs of adjacent teeth satisfy the criterion for adjacent teeth. Responsive to satisfying the criterion, virtual filler module 2050 may generate a virtual filler for identified pairs of adjacent teeth, as described herein. Adjacent teeth 733 is an example of two adjacent teeth that fulfill the criterion and will be used in the following description to describe the formation of a virtual filler for adjacent teeth.

Figure 8:
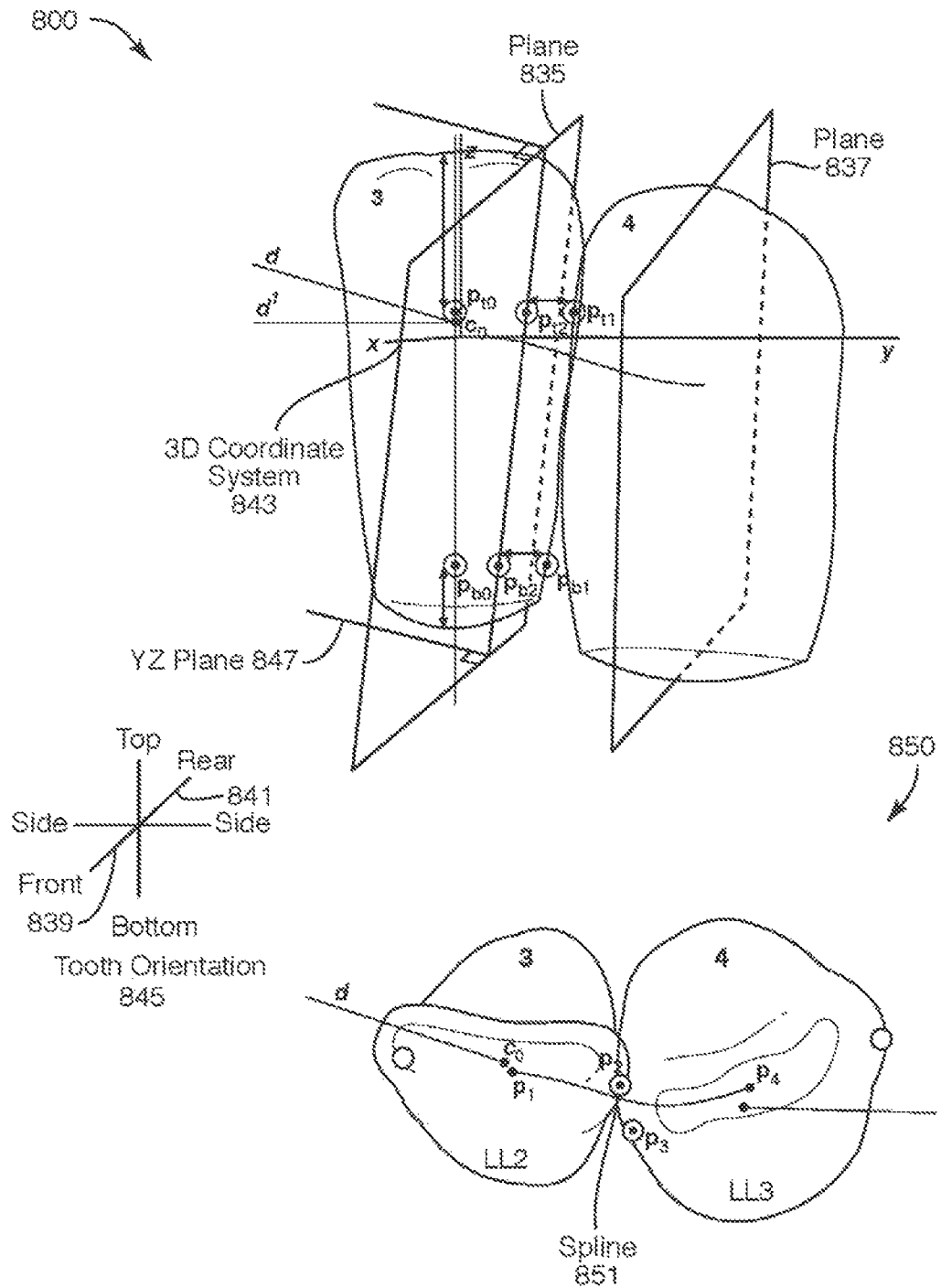
FIG. 8 illustrates a plane that intersects a front and a rear of a tooth of two adjacent teeth, in accordance with some embodiments.

FIG. 8 illustrates a plane that intersects a front and a rear of a tooth of two adjacent teeth, in accordance with some embodiments. Diagram 800 and 850 show adjacent teeth 733 of FIG. 7 from a front-facing perspective and a top-down perspective, respectively. Adjacent teeth 733 are also referred to as tooth 3 and tooth 4. In embodiments, a virtual filler module 2050 detects that tooth 3 is adjacent tooth 4 in the virtual model 701. In embodiments, virtual filler module 2050 determines a plane 835 (e.g., first plane) that intersects a front 839 and a rear 841 of tooth 3 and a plane 837 (e.g., second plane) that intersects the front and rear of tooth 4. Tooth orientation 845 is provided to illustrate the relative orientation of tooth 3 and tooth 4 with respect to diagram 800. It may be appreciated that the tooth orientation 845 may be used throughout the disclosure to describe the relative orientation of respective teeth, i.e., top surface, bottom surface, rear 841 surface, front 839 surface, and side surfaces. It may be noted that tooth 3 and 4 as described with respect to FIGS. 7-12 refer to the respective teeth (e.g., adjacent teeth 733) of virtual model 701B of dental arch of FIG. 7.

In embodiments, determining a plane 835 that intersects a front 839 (i.e., front surface) and a rear 841 (i.e., rear surface) of tooth 3 includes generating a three-dimensional (3D) coordinate system 843 with respect to the tooth 3. The z-axis of the 3D coordinate system 843 intersects a bottom portion and a top portion of the tooth 3 (see tooth orientation 845). The y-axis of the 3D coordinate system 843 extends in a direction of the second tooth. Virtual filler module 2050 determines a first point (e.g., $P_{t2}$) and a second point (e.g., $P_{b2}$) within the tooth 3. The first point (e.g., $P_{t2}$) and a second point (e.g., $P_{b2}$) lay along the yz-plane 847. Virtual filler module 2050 may generate plane 835 so that it contains the first point (e.g., $P_{t2}$) and a second point (e.g., $P_{b2}$) and is perpendicular to yz-plane 847. It may be noted that similar operations may be performed on tooth 4 to find plane 837.

In embodiments, determining a plane 835 that intersects a front 839 and a rear 841 of tooth 3 includes generating a three-dimensional (3D) coordinate system 843 with respect to the tooth 3. Virtual filler module 2050 may generate a spline 851 using at least four control points: two points at the centers of tooth 3 and tooth 4 ($P_1$ and $P_4$, respectively) and the proximal points ($P_2$ and $P_3$). The proximal points may be a point on each tooth 3 and 4 that would touch or otherwise align if tooth 3 and 4 where properly aligned (e.g., target positions). Of note, "d" may be the inverse of spline direction and "$c_0$" may be the center of the tooth offset from the top surface of the tooth (e.g., ⅓ the distance from top to bottom of the tooth). A line through $c_0$ may be drawn that is parallel the z-axis. Virtual filler module 2050 may find points ($P_{b0}$ and $P_{t0}$) that intersect the top and bottom surface of tooth 3 and lay along a line drawn through $c_0$. Point $P_{t0}$ may be shifted down from the top of tooth 3 (e.g., shift of 7.0 mm but no more than ⅓ tooth height). Point $P_{b0}$ may be shifted from the bottom of tooth (e.g., shift of 1.5 mm but no more than ⅓ tooth height). Virtual filler module 2050 may project direction d onto the tooth xy-plane obtaining direction d'. Virtual filler module 2050 may project $p_{t0}$ and $p_{b0}$ onto the surface of tooth 3 along d' to obtain points $p_{t1}$ and $p_{b1}$. Points $p_{t1}$ and $p_{b1}$ may be shifted towards the center of tooth 3 along d' to obtain points $p_{t2}$ and $p_{b2}$. For example, points $p_{t1}$ and $p_{b1}$ may be shifted towards the center 20% of tooth width along d' to obtain points $p_{t2}$ and $p_{b2}$. Plane 835 may be generated so that plane 835 contains points $p_{t2}$ and $p_{b2}$ and is perpendicular to plane containing $p_{t2}$, $p_{b2}$ and d' (e.g., yz-plane 847). It may be noted that similar operations may be performed on tooth 4 to find plane 837.

Figure 9:
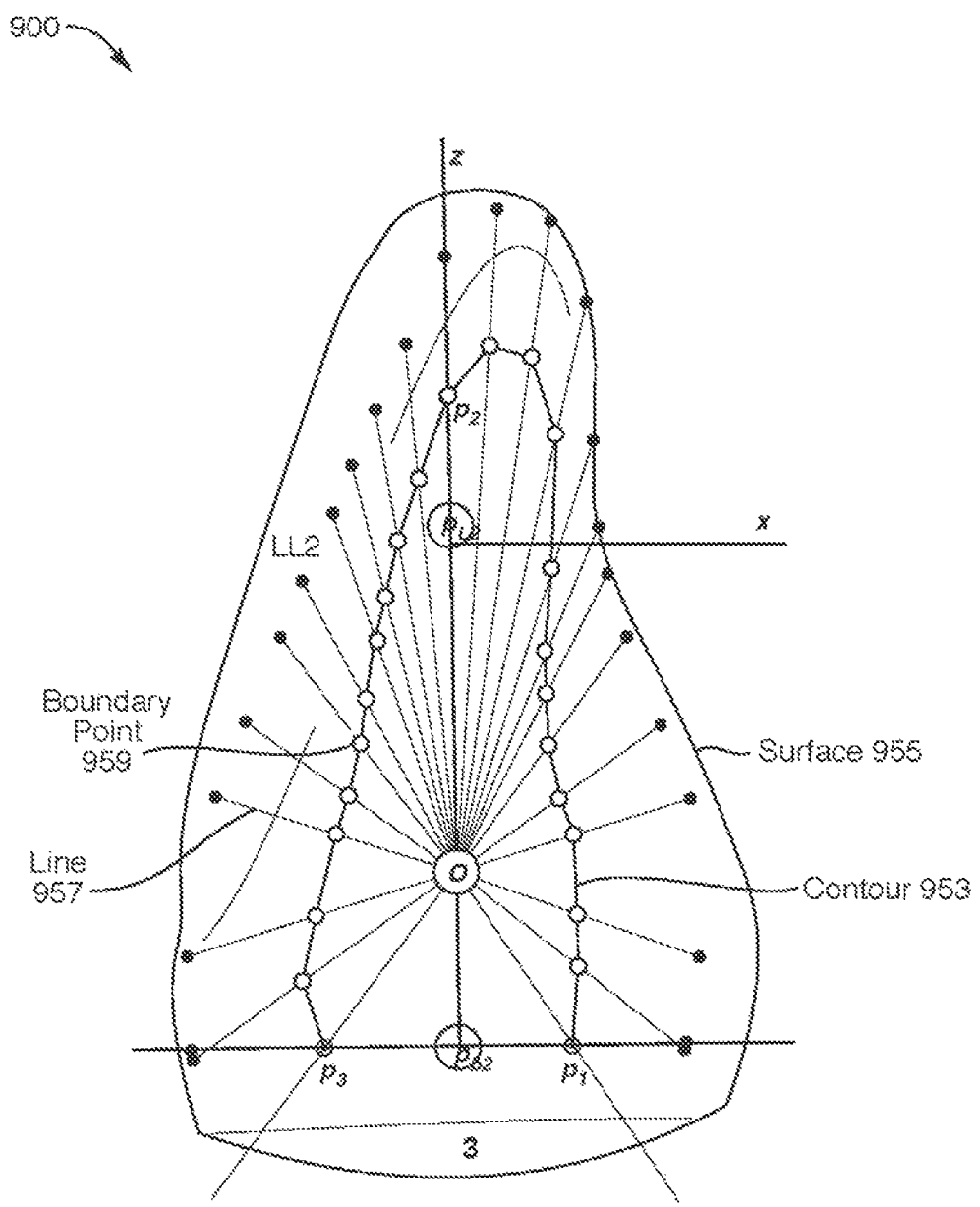
FIG. 9 illustrates a contour on a plane that intersects a front and a rear of a tooth of two adjacent teeth, in accordance with some embodiments.

FIG. 9 illustrates a contour on a plane that intersects a front and a rear of a tooth of two adjacent teeth, in accordance with some embodiments. Diagram 900 shows contour 953 that is projected on plane 834 of FIG. 8 within tooth 3. It may be noted that for purposes of illustration, the contour 953 of tooth 3 is described, and the operations described herein may be applied to generate another contour for tooth 4. It may also be noted that the contours, such as contour 953, may form the sides of the virtual filler, and are approximately aligned parallel with the sides of the respective tooth. In embodiments, virtual filler module 2050 generates a first contour (e.g., contour 953) within tooth 3 and on the plane 834 and a second contour within tooth 4 and on plane 837 of FIG. 8. In embodiments, generating a contour 953 within tooth 3 where contour 953 is on plane 834 includes determining a third point (e.g., origin point "o") that is between the first point (e.g., $p_{t2}$) and the second point ($p_{b2}$) and on the yz-plane 847 of FIG. 8. Virtual filler module 2050 may determine multiple lines (e.g., line 957) from the third point (e.g., point "o") to a surface 955 of tooth 3. Each of the multiple lines extends from the third point (e.g., point "o") to a different point on the surface 955 of the tooth 3. Virtual filler module 2050 determines multiple boundary points (e.g., boundary point 959). Each of the boundary points are located on a respective one of the lines a distance from the surface 955 of tooth 3. Virtual filler module 2050 connects the boundary points to form the contour 953.

In some embodiments, virtual filler module 2050 may determine the contour 953 by letting the z-axis be a projection of tooth basis z-axis onto plane 835. Virtual filler module 2050 may let the y-axis plane be the plane normal to plane 835 and pointing from the tooth 3 to tooth 4. Virtual filler module 2050 may define an operator (e.g., project (point, angle)) as follows: Virtual filler module 2050 may take a ray laying in the plane 835 with origin in point (e.g., point origin "o") and having an angle between x axis and ray's direction. Point may refer to the projection center, while angle may refer to arbitrary parameters (e.g., selected by an administrator). Virtual filler module 2050 projects the ray onto the surface 955 of the tooth 3 and takes the projection point (e.g., point that intersects the surface 955 of tooth 3). Virtual filler module 2050 may shift the projection point back towards point a distance from the surface 955 but not more than a proportion of the distance from point to the surface 955 along the ray.

In embodiments, virtual filler module 2050 may obtain points $p_1$=project ($p_{b2}$, 0), $p_2$=project ($p_{b2}$, $\pi/2$), and $p_3$=project ($p_{b2}$, $\pi$). Virtual filler module 2050 may find the projection center o=HEIGHT_PROPORTION*$p_{b2}$+(1−HEIGHT_PROPORTION)*$p_{t2}$, where HEIGHT_PROPORTION=⅓. Virtual filler module 2050 lets $\alpha_i$ be the angle between the ray o–$p_i$ and the x-axis. Virtual filler module 2050 obtains other boundary points using a recursive algorithm as follows: take two angles $\beta_1$ and $\beta_2$ (the algorithm is invoked twice for pairs $\alpha_1$, $\pi$ and $\pi$, $\alpha_3$) with corresponding boundary points $b_1$ and $b_2$. If cos ($\beta_2 - \beta_1$)<MAX_COS=0.99 and $|b_2 - b_1|$>MESH_EDGE_LENGTH=1 mm, then calculate $\beta = (\beta_2 - \beta_1)$ and a new boundary point b=project (o, $\beta$). The same algorithm is applied to angle pairs $\beta_1$, $\beta$ and $\beta$, $\beta_2$.

Figure 10:
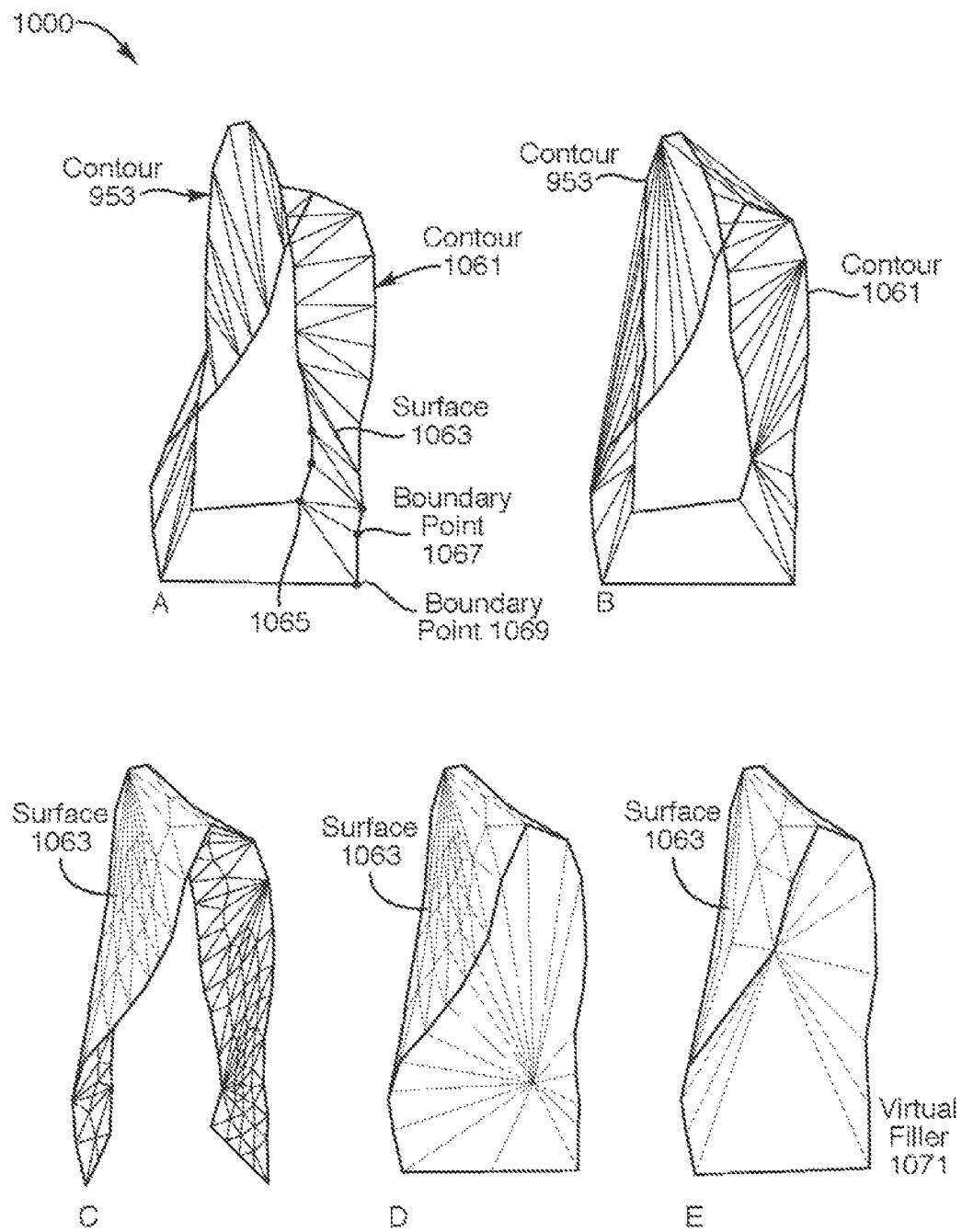
FIG. 10 illustrates a construction of a surface of a virtual filler, in accordance with some embodiments.

FIG. 10 illustrates a construction of a surface of a virtual filler, in accordance with some embodiments. Diagram 1000 shows multiple stages (e.g., stages A-E) of constructing a surface of a virtual filler 1071 by connecting contour 953 of tooth 3 to contour 1061 of tooth 2. It may be noted that some or all the stages may be implemented in some embodiments. In one embodiment, connecting contour 953 to contour 1061 to construct a surface 1063 of a virtual filler 1071 includes connecting boundary points (e.g., boundary point 1065) of contour 953 with boundary points of contour 1061 (e.g., stage A). Virtual filler module 2050 may perform stage C to smooth surface 1063 of the virtual filler 1071 (e.g., reduce rough edges or vertices). Virtual filler module 2050 may perform stage D to fill the surface 1063 of virtual filler 1071. In embodiments, the connecting of the contours 953 and 1061 and generation of the surface forms or completes the geometry of virtual filler 1071.

In some embodiments, to connect contour 953 to the contour 1061 to construct a surface 1063 of the virtual filler 1071, virtual filler module 2050 may connect the boundary points on contour 953 with the boundary points on contour 1061 so that the bottom boundary points (e.g., boundary point 1065 and boundary point 1069) are pairwise connected and the other boundary points (e.g., boundary point 1067) are paired based on the distance between the boundary points (e.g., stage A). At stage B, the connecting edges are flipped until the surface 1063 has a minimal surface area. Flipping a connecting edge may refer to replacing an edge by another edge. For example, given two adjacent triangles ABC and BCD (sharing edge BC), edge BC may be flipped by replacing edge BC with another edge AD. At stage C, the surface 1063 of virtual filler 1071 is refined and smoothed. In embodiments, refined may include splitting in half all edges longer than a threshold (e.g., 1 mm), starting from the longest edge until there are no edges longer than the threshold. In embodiments, smoothing may include multiple iterations (e.g., 10 iterations) of smoothing, such as Laplacian smoothing. At stage D, the virtual filler 1071 is filled. At stage E, the surface 1063 of virtual filler 1071 is decimated with a mesh tolerance (e.g., mesh tolerance=0.1 mm) to remove extra vertices. In embodiments, decimation of a mesh may include removing some vertices so that the surface 1063 is similar to the surface 1063 at stage C, for example. In embodiments, the completion of one or more of the stages A-D forms or completes the geometry (e.g. initial geometry) of virtual filler 1071. In other embodiments, the geometry of the virtual filler 1071 may be further updated or modified, as described below.

In some embodiments, the geometry of the virtual filler 1071 may be modified in view of a clinical feature. In an embodiment, virtual filler module 2050 may detect a clinical feature on tooth 3 or tooth 4. Virtual filler module 2050 may determine if the clinical features contact the virtual filler 1071. Responsive to determining the clinical feature contacts the virtual filler 1071, virtual filler module 2050 may remove the part of the virtual filler 1071 that is in contact with the clinical feature.

In some embodiments, the geometry of the virtual filler 1071 may be modified in view of an incisal area. In an embodiment, virtual filler module 2050 may determine an incisal area on tooth 3 or tooth 4. Virtual filler module 2050 may determine whether the incisal area contacts the virtual filler 1071. Responsive to determining that the incisal area contacts the virtual filler 1071, virtual filler module 2050 may remove the part of the virtual filler 1071 that contacts the incisal area.

Figure 11:
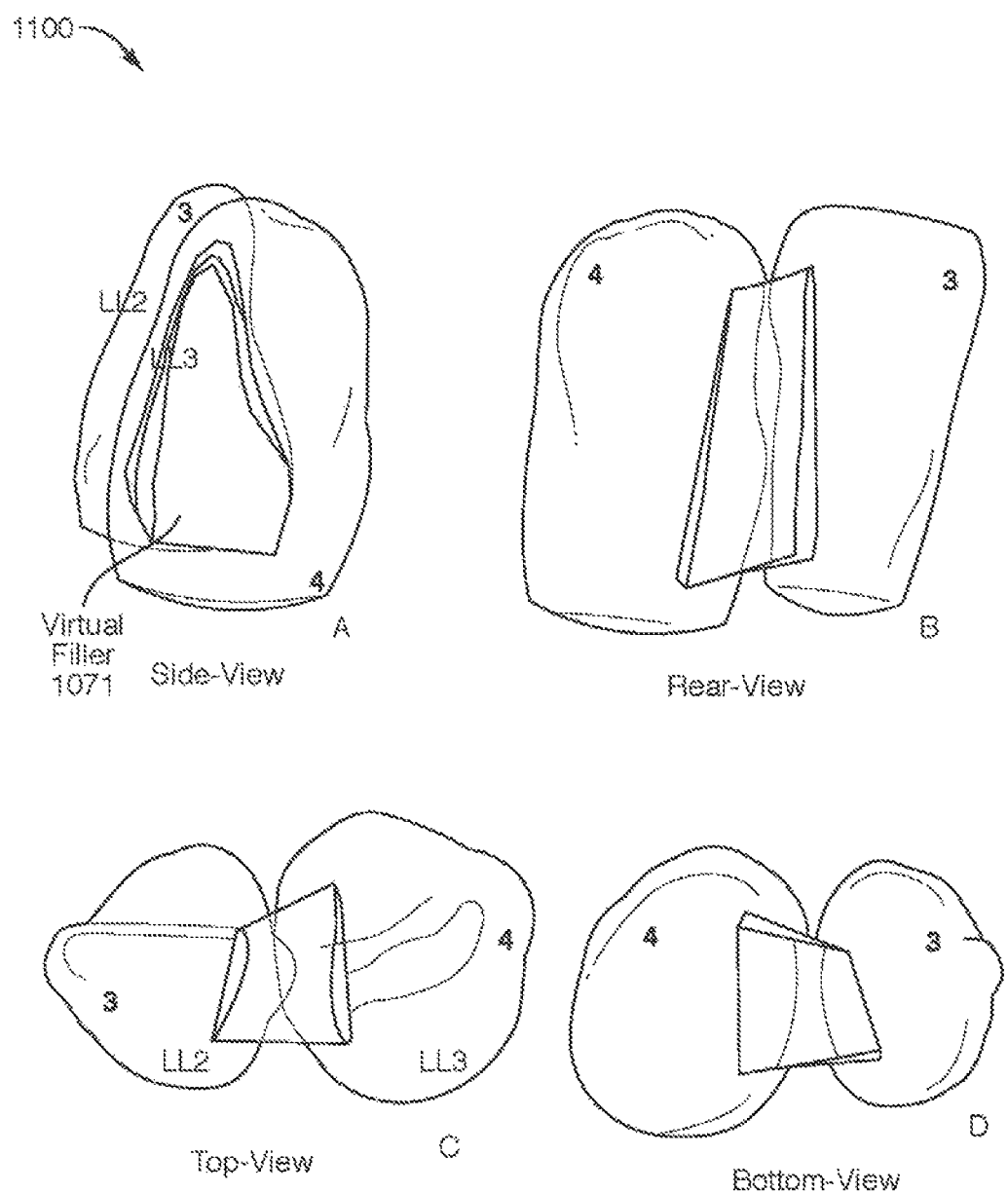
FIG. 11 illustrates a geometry of a virtual filler for adjacent teeth, in accordance with some embodiments.

FIG. 11 illustrates a geometry of a virtual filler for adjacent teeth, in accordance with some embodiments. Diagram 1100 illustrates multiple views of the virtual filler 1071 of FIG. 10 orientated within tooth 3 and tooth 4. Diagram 1100A shows a side-view of virtual filler 1071 with tooth 3 in front of tooth 4. It may be noted that the virtual filler 1071 is encased by tooth 3 and tooth 4 on the respective ends of the virtual filler 1071. The gap between the tooth 3 and tooth 4 may be an area of the virtual filler 1071 that is exposed externally. Diagram 11008 show a rear-view of the virtual filler 1071. Diagram 1100C shows a top-view of virtual filler 1071 and diagram 1100D shows the bottom-view of the virtual filler 1071. It may be noted that diagram 1100 illustrates the geometry (e.g., shape) of the virtual filler 1071, which may also include the location of the virtual filler 1071 with respect to tooth 3 and tooth 4 as well as the location of virtual filler 1071 with respect to the greater dental arch. In some embodiments, the location of the virtual filler 1071 in the virtual model may be determined based on the plane 835 and 837 of FIG. 8.

It may be noted that the geometry (e.g., sides of the virtual filler 1071 are located within the tooth 3 and 4) allows virtual filler 1071 to be used for the fabrication of multiple sequential physical molds in a series. For example, as the teeth shift position from one physical mold to the next, the gap between the teeth also changes. Virtual filler 1071 may be re-used as the gap changes. For instance, as the gap between the teeth increases more of virtual filler 1071 is exposed.

Figure 12:
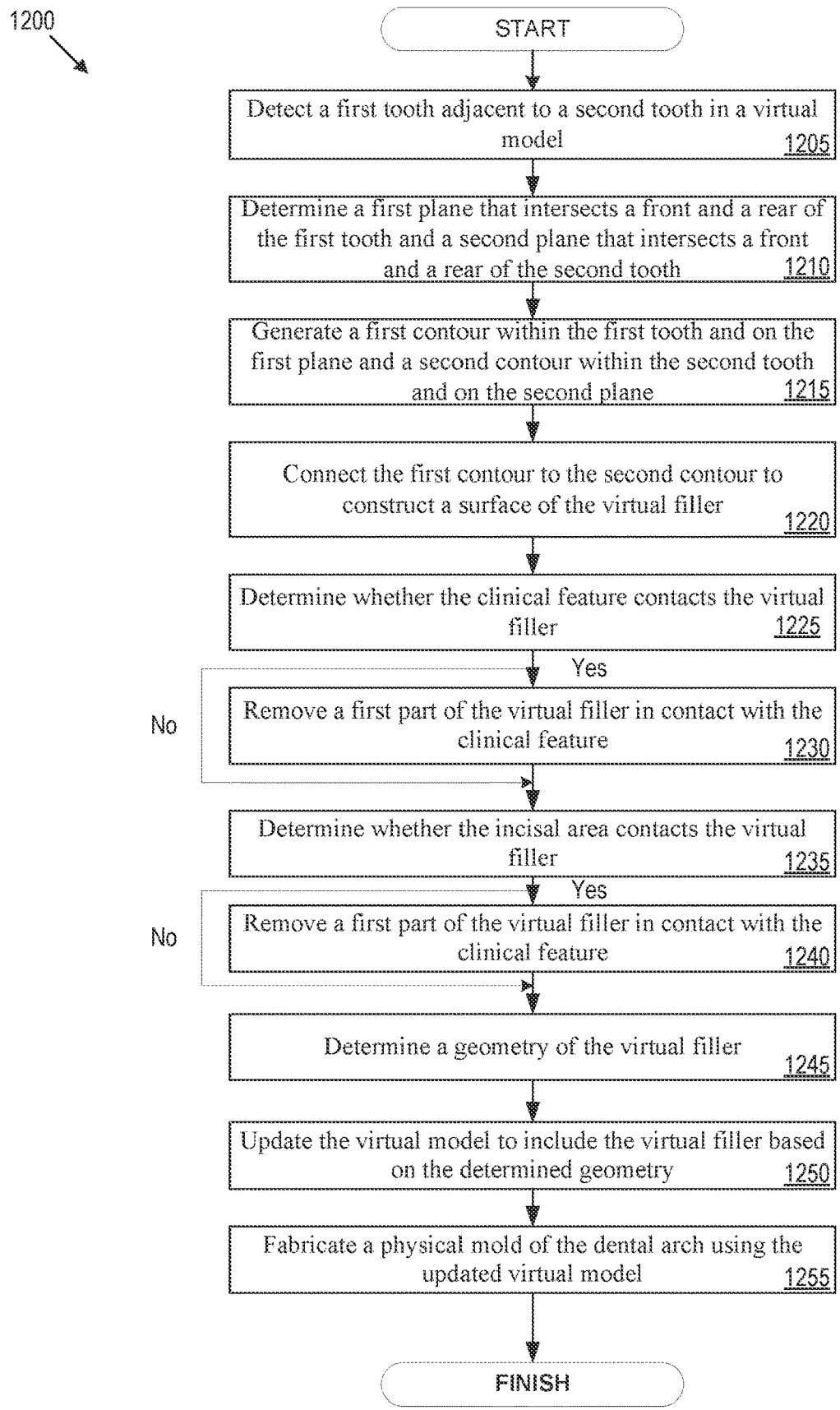
FIG. 12 illustrates a flow diagram for a method of creating a virtual filler for adjacent teeth, in accordance with one embodiment.

FIG. 12 illustrates a flow diagram for a method of creating a virtual filler for adjacent teeth, in accordance with one embodiment. One or more operations of method 1200 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 1200 may be performed by a processing device executing a computer aided drafting (CAD) program or module such as a virtual filler module 2050. Elements of the previous figures may be used to help illustrate method 1200. It may be appreciated that the in some implementations, method 1200 may include the same, different, fewer, or greater operations performed in any order.

In an embodiment, processing logic implementing method 1200 begins at block 1205 where processing logic detects a first tooth adjacent to a second tooth in a virtual model. At block 1210, processing logic determines a first plane that intersects a front and a rear of the first tooth and a second plane that intersects a front and a rear of the second tooth (e.g., as described with reference to FIG. 8). At block 1215, processing logic generates a first contour within the first tooth and on the first plane and a second contour within the second tooth and on the second plane (e.g., as described with reference to FIG. 9). The first contour and the second contour are respective sides of the virtual filler. At block 1220, processing logic connects the first contour to the second contour to construct a surface of the virtual filler (e.g., as described with reference to FIG. 10).

At block 1225, processing logic detects a clinical feature and determines whether the clinical feature contacts the virtual filler. Responsive to determining that the clinical feature does not contact the virtual filler, processing logic moves to block 1235. Responsive to determining that the clinical feature does contact the virtual filler, processing logic moves to block 1230. At block 1230, processing logic removes a first part of the virtual filler in contact with the clinical feature (e.g., as described with reference to FIG. 10).

At block 1235, processing logic detects an incisal area of the first tooth and the second tooth and determines whether the incisal area contacts the virtual filler. Responsive to determining that the incisal area does not contact the virtual filler, processing logic moves to block 1245. Responsive to determining that the incisal area does contact the virtual filler, processing logic moves to block 1240. At block 1240, processing logic, removes the second part of the virtual filler in contact with the incisal area (e.g., as described with reference to FIG. 10).

At block 1245, processing logic determines the geometry of the virtual filler. At block 1250, processing logic updates the virtual model to include the virtual filler based on the determined geometry. At block 1255, processing logic fabricates a physical mold of the dental arch using the updated virtual model. The physical mold includes material in an area of the virtual filler.

Figure 13:
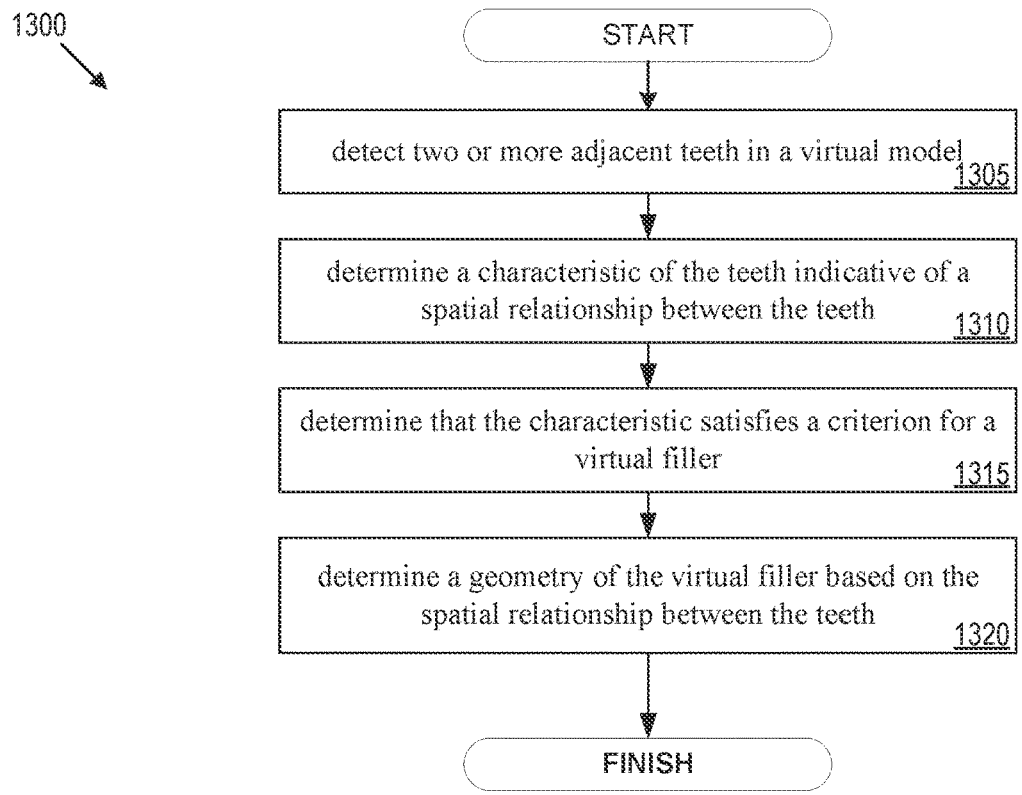
FIG. 13 illustrates a flow diagram for a method of creating a virtual filler for adjacent teeth or crowded teeth, in accordance with one embodiment.

FIG. 13 illustrates a flow diagram for a method of creating a virtual filler for adjacent teeth or crowded teeth, in accordance with one embodiment. One or more operations of method 1300 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 1300 may be performed by a processing device executing a computer aided drafting (CAD) program or module such as a virtual filler module 2050. Elements of the previous figures may be used to help illustrate method 1300. It may be appreciated that the in some implementations, method 1300 may include the same, different, fewer, or greater operations performed in any order.

In an embodiment, processing logic performing the method 1300 begins at block 1305 to detect two or more adjacent teeth in a virtual model. At block 1310, processing logic determines a characteristic of the teeth indicative of a spatial relationship between the teeth, as described above. For example, the characteristic may be a distance between the surfaces of two teeth. At block 1315, processing logic determines that the characteristic satisfies a criterion for a virtual filler, as described above. For example, processing logic may determine that the characteristics satisfy a criterion for crowded teeth or adjacent teeth. At block 1315, processing logic determines a geometry of the virtual filler based on the spatial relationship between the teeth. For example, processing logic may determine the geometry of the virtual filler for crowded teeth or adjacent teeth, as described herein. For adjacent teeth that satisfy a first adjacent teeth virtual filler criterion, method 1200 may be performed to generate a virtual filler. For adjacent teeth that satisfy a second crowded teeth virtual filler criterion, method 600 may be performed to generate a virtual filler. Notably, method 1200 may be performed to generate one or more virtual fillers for a virtual 3D model of a dental arch and method 600 may be performed to generate one or more virtual fillers for the same dental arch.

Figure 14:
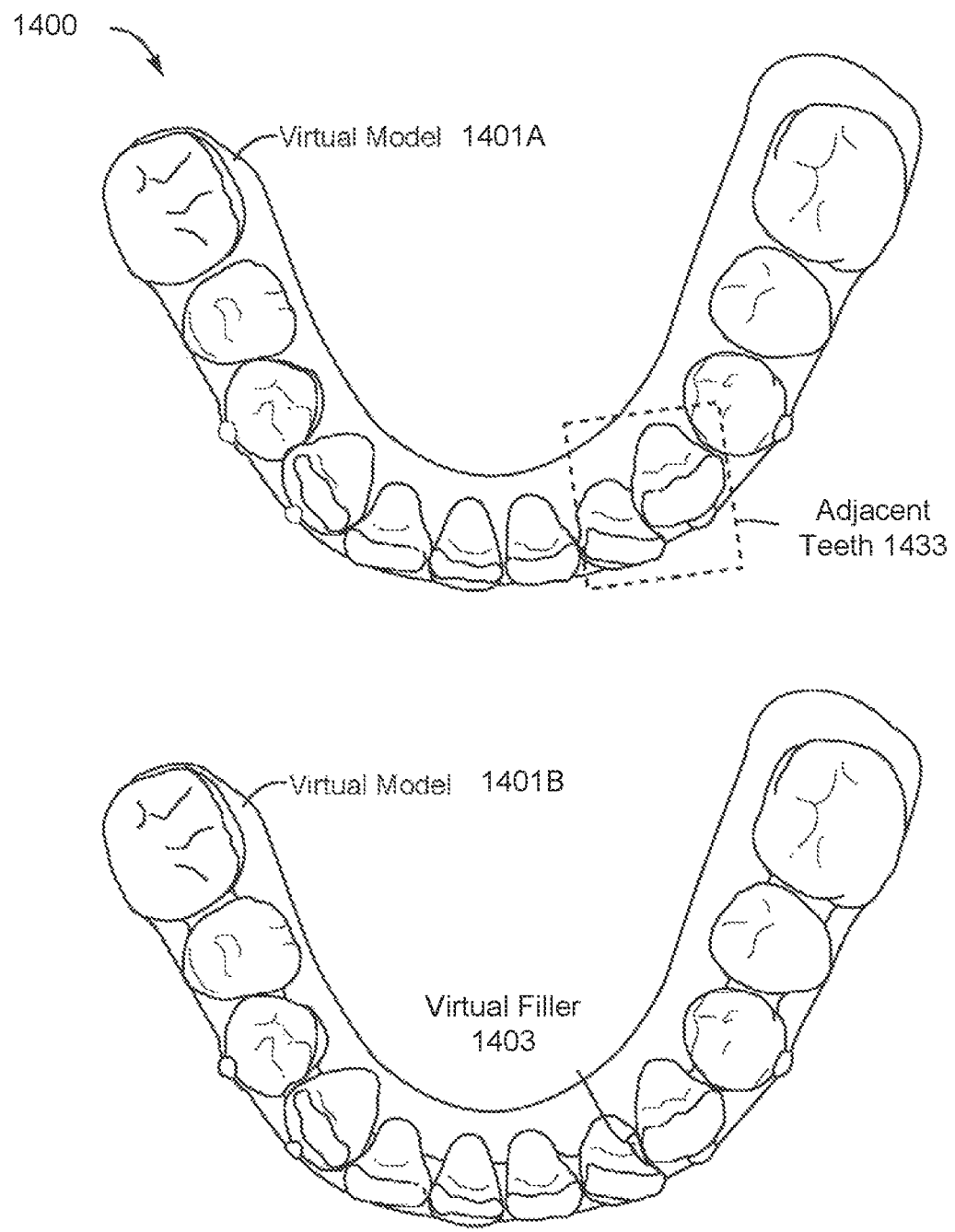
FIG. 14 illustrates a virtual model of dental arches with at least two adjacent teeth with and without virtual fillers, in accordance with embodiments.

FIG. 14 illustrates a virtual model of dental arches with at least two adjacent teeth with and without virtual fillers, in accordance with embodiments. Diagram 1400 shows a virtual model 1401A of a dental arch without virtual fillers and a virtual model 1401B of a dental arch with virtual fillers, such as virtual filler 1403. In embodiments, two or more adjacent teeth (or "at least two adjacent teeth") may refer to crowded teeth or adjacent teeth. As noted above, adjacent teeth may refer to any two teeth that are directly adjacent to one another (i.e., no intervening teeth). In embodiments, determining two or more adjacent teeth in a virtual model can be based on one or more characteristics or criteria, as described above. Similarly, determining whether two or more adjacent teeth are crowded teeth can be based on one or more characteristics or criteria, as described above.

In embodiments, determining that two or more adjacent teeth in a virtual model are adjacent teeth can be based on characteristics of the teeth. In embodiments, the distance between the two adjacent teeth (also referred to as "adjacent teeth" herein, unless otherwise described) may be a characteristic of the adjacent teeth. In embodiments, adjacent teeth that are directly adjacent teeth may be another characteristic. In some embodiments, the distance between the adjacent teeth may be compared to a criterion, such as a threshold (e.g., distance in millimeters (mm)), to determine whether the teeth are adjacent teeth. For example, two teeth that are directly adjacent and have a distance between the two teeth of less than X millimeters may be considered adjacent teeth. It may be noted that all the teeth of virtual model 1401A may be checked to determine whether the pairs of adjacent teeth satisfy the criterion for adjacent teeth (and/or crowded teeth). Responsive to satisfying the criterion, virtual filler module 2050 may generate a virtual filler for identified pairs of adjacent teeth (and crowded teeth), as described herein. Adjacent teeth 1433 are an example of two adjacent teeth that fulfill the criterion and will be used in the following description to describe the formation of a virtual filler for adjacent teeth according to an embodiment.

In embodiments, determining two more adjacent teeth in a virtual model are crowded teeth can be based on characteristics of the teeth. In embodiments, determining that the two or more adjacent teeth are crowded teeth is based on determining that the two or more adjacent teeth include at least three teeth that satisfy a crowding criterion indicative of an amount of overlap between the teeth. Characteristics and criteria for determining crowded teeth is further described above at least with respect to FIGS. 2-6B. For purposes of illustration, rather than limitation FIG. 14 shows adjacent teeth. It can be noted that the following processes can be applied to adjacent teeth or crowded teeth. In some embodiments, separate criteria for identifying crowded teeth may not be used. That is, the criteria for adjacent teeth may be used to detect the adjacent relationship of three or more teeth that may constitute crowded teeth (e.g., since pairs of teeth of the crowded teeth may be adjacent teeth).

Figure 15:
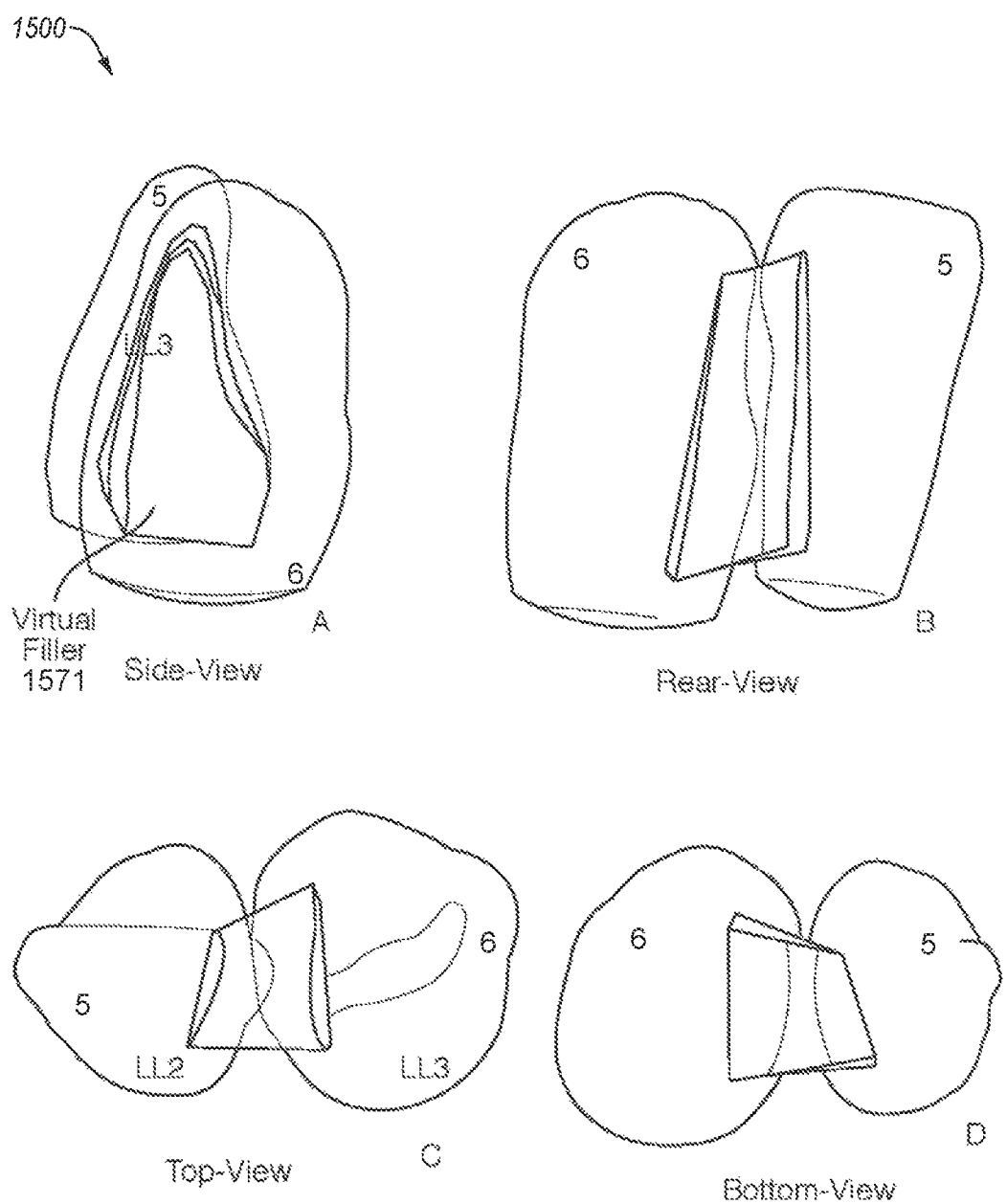
FIG. 15 illustrates an insertion of a virtual filler in the virtual model, in accordance with some embodiments.

FIG. 15 illustrates an insertion of a virtual filler in the virtual model, in accordance with some embodiments. It can be noted that the virtual model may be a virtual model of a dental arch (not shown). Diagram 1500 illustrates multiple views of the virtual filler 1571 orientated within tooth 5 and tooth 6. It may be noted that tooth 5 and 6 as described herein can refer to the respective teeth (e.g., adjacent teeth 1433) of virtual model 1401A of dental arch of FIG. 14. Diagram 1500A shows a side-view of virtual filler 1571 with tooth 5 in front of tooth 6. It may be noted that the virtual tooth 1571 is encased by tooth 5 and tooth 6 on the respective ends of the virtual filler 1071. The gap between the tooth 5 and tooth 6 may be an area of the virtual filler 1071 that is exposed externally. In embodiments, each side of the virtual filler 1571 is located within one of tooth 5 and tooth 6. Diagram 1500B show a rear-view of the virtual filler 1571. Diagram 1500C shows a top-view of virtual filler 1571 and diagram 1500D shows the bottom-view of the virtual filler 1571.

In some embodiments, the virtual filler 1571 may be the same as virtual filler 1071 of FIG. 11 and generated using the same operations as described above with respect to FIGS. 7-12. In other embodiments, virtual filler 1571 may be similar to virtual filler 1071 but is generated using a subset of the operations as described above with respect to FIGS. 7-12. For example, virtual filler 1571 may be similar to virtual filler 1071 at stage A of FIG. 10, where the additional stages B-E are not performed on virtual filler 1071.

In some embodiments, virtual filler 1571 may be selected from one or more predetermined shapes. For example, the shape may be a cylinder (e.g., tube), rectangle, cube, other polygon, or other geometric shape. In some embodiments, the predetermined shapes may have varies sizes and contours, and may be selected for insertion between adjacent teeth so that at least the each side of the virtual filler 1571 is located or encased within a respective one of tooth 5 or tooth 6. In some embodiments, the predetermined shapes may be selected for insertion between adjacent teeth so that at least a portion of the top and bottom of the virtual filler 1571 is located or encased within tooth 5, and another portion of the top and bottom of the virtual filler 1571 is located or encased within tooth 6. In some embodiments, virtual filler 1571 may be a predetermined shape and be inserted using one or more operations as described above with respect to virtual filler 1071 of FIGS. 7-12. For example, plane 835 and 837 of FIG. 8 may be generated and a predetermine shape that fits between plane 835 and 837 can be selected and inserted between tooth 5 and tooth 6. Similarly, the sides, the top, or bottom can be located or encased within the adjacent teeth as described above.

In embodiments where the two or more adjacent teeth are crowded teeth, a virtual filler (similar or the same as virtual filler 1571) can be inserted between all pairs or adjacent teeth of the crowded teeth. For example, if the crowded teeth included tooth 5, tooth 6, and tooth 7 (not shown), a virtual filler can be inserted between tooth 5 and tooth 6, between tooth 5 and tooth 7, and between tooth 6 and tooth 7.

The virtual fillers that are added between the teeth may be initial virtual fillers, and may not reflect a final size and/or shape of the virtual fillers. One or more additional operations may be performed to adjust the size and/or shape of the virtual fillers. Additionally, in the case for crowded teeth, multiple initial virtual fillers may be merged, and then operations may be performed to change a size and/or shape of the merged virtual fillers.

Figure 16:
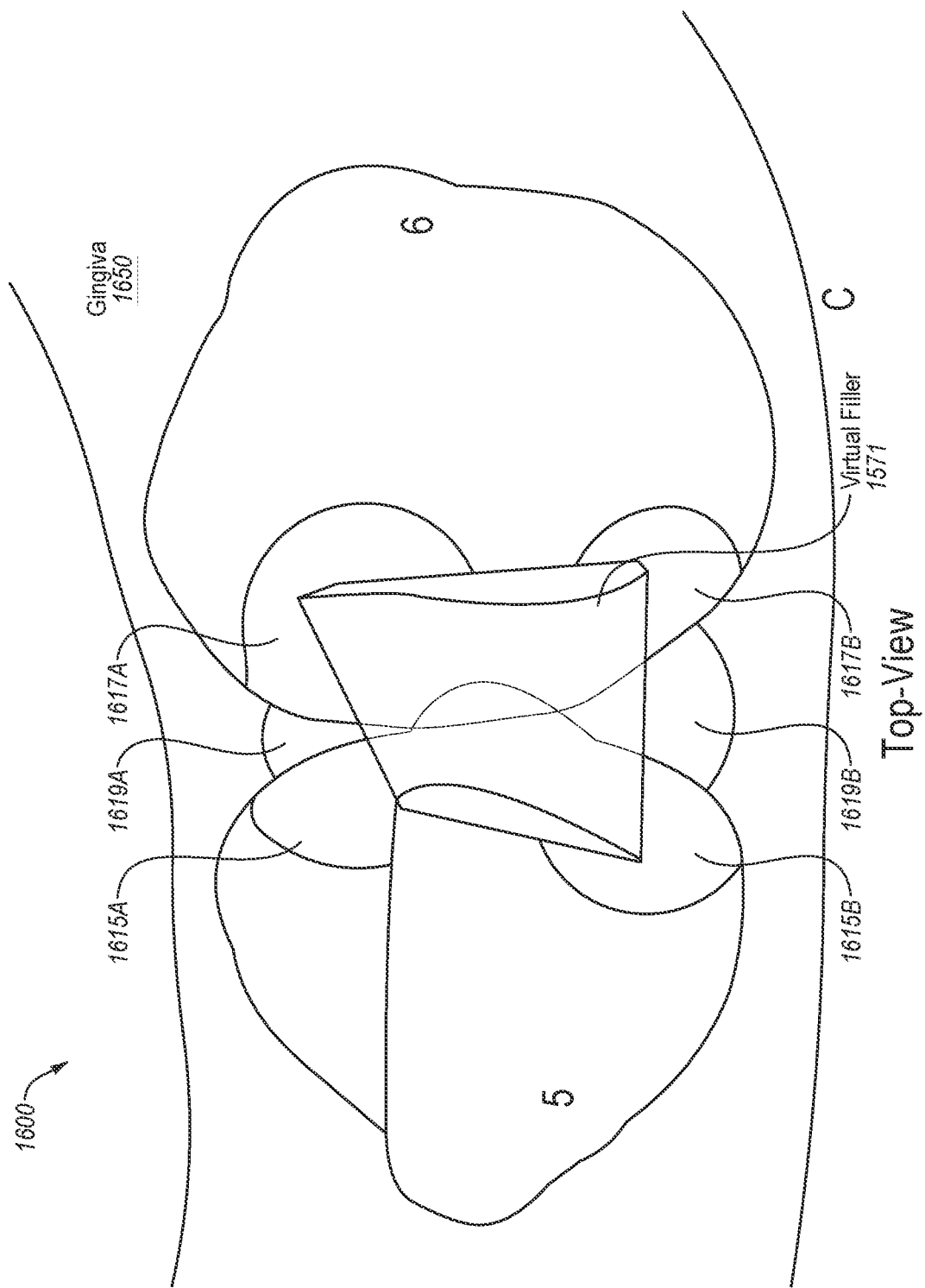
FIG. 16 illustrates a selection of points in the virtual model, in accordance with some embodiments.

FIG. 16 illustrates a selection of points in a virtual model, in accordance with some embodiments. In embodiments, point in the virtual filler can be selected to help generate a 3D object that is used to create an updated or final virtual filler. The selected points can be used in a subsequent operation to generate and manipulate the 3D object. As illustrated in diagram 1600, tooth 5 and tooth 6 are adjacent teeth. A coronal portion of tooth 5 and tooth 6 extends from the gingiva 1650. In some embodiments, the selected points (i.e., countably additive points or scalar values) in the virtual model can include points 1615A and 1615B (generally referred to "points 1615" herein) that are points on the surface of tooth 5. In some embodiments, the selected points in the virtual model can include points 1617A and 1617B (generally referred to "points 1617" herein) that are points on the surface of tooth 6. In some embodiments, the selected points in the virtual model can include points 1619A and 1619B (generally referred to "points 1619" herein) that are points on the surface of the gingiva 1650. In some embodiments, the selected points in the virtual model can include points on the virtual filler 1571 (not illustrated).

In some embodiments, selecting points on the surface of tooth 5 includes selecting points on the surface of tooth 5 that are a threshold distance (e.g., 1.5 mm) from virtual filler 1571. Selecting points on the surface of tooth 6 may include selecting points on the surface of tooth 6 that are a threshold distance (e.g., 1.5 millimeters (mm)) from virtual filler 1571. In some embodiments, different distance thresholds may be used for the distance between points on adjacent teeth and the distance between points on a tooth and points on a virtual filler. In embodiments, selecting points on the surface of tooth 5 includes selecting points on the surface of tooth 5 that are within a threshold distance (e.g., 3 mm) from the adjacent tooth 6. Selecting points on the surface of tooth 6 may include selecting points on the surface of tooth 6 that are within a threshold distance from the adjacent tooth 5. In embodiments, selecting points on the surface of tooth 6 includes selecting points on the surface of tooth 6 that are closer than a first threshold distance from tooth 5 and that are closer than a second threshold distance from the virtual filler. Similarly, selecting points on the surface of tooth 5 includes selecting points on the surface of tooth 5 that are closer than a first threshold distance from tooth 6 and that are closer than a second threshold distance from the virtual filler. The first threshold distance may be different from the second threshold distance. For example, the first threshold distance may be greater than the second threshold distance.

In embodiments, selecting points on the surface of the gingiva 1650 includes selecting points on the surface of the gingiva 1650 that are within a threshold distance from the virtual filler 1571. In some embodiments, one or more of the above thresholds can be adjusted. In some embodiments, larger thresholds can be selected (e.g., to include more points) if more smoothing (e.g., larger radius of curvature) is desired for the updated virtual filler (as described below). In embodiments, smaller thresholds may be selected if less smoothing (smaller radius of curvature) is desired for the updated virtual filler.

In embodiments where the two or more adjacent teeth are crowded teeth, the points on the surface of each of the crowded teeth can be selected in a similar manner as described above with respect to FIG. 3 and FIG. 15. Alternatively, for crowded teeth the same point selection technique may be applied that is applied for adjacent teeth. However, this point selection technique may be applied for each pair of teeth of the crowded teeth. In embodiments where the two or more adjacent teeth are crowded teeth, selected points in the virtual model can include points on each of the virtual fillers inserted between each pair of adjacent teeth of the crowded in a similar manner as described above. In embodiments where the two or more adjacent teeth are crowded teeth, selected points in the virtual model can include points on the surface of the gingiva 1650 in a similar manner as described above. For example, the selected points on the surface of the gingiva 1650 can include points that are within a threshold distance from each of the virtual fillers inserted between the crowded teeth.

In some embodiments, the selected points for both adjacent teeth and crowded teeth may be adjusted to account for clinical features on the teeth. As noted above, a clinical feature may be a foreign object located on or attached to a tooth. For example, a clinical feature may include a filling, a bridge, a bracket (of braces), and so forth. In embodiments, a clinical feature may be detected on at least one of the teeth. In embodiments, a determination may be made whether the clinical feature contacts any of the selected points in the virtual model. Responsive to determining that a clinical feature contacts any of the selected points in the virtual model, the affected points may be removed from consideration. For example, if a clinical feature were determined to overlap some of points 1617B (which is not the case in diagram 1600), the overlapped points can be removed from the selected points so that there is no overlap between clinical feature and points 1617B. Responsive to determining that a clinical feature does not contact the selected points in the virtual model, the selected points are not removed.

In some embodiments, the selected points for both adjacent teeth and crowded teeth may be adjusted to account for incisal areas (also referred to as "occlusal areas" herein) of the teeth. As noted above, an incisal area may be an area of the tooth that is used for eating or an area that contacts with an opposing tooth in the opposing dental arch. In embodiments, an incisal area of each tooth of the adjacent teeth or crowded teeth may be determined. In embodiments, a determination is made whether the incisal area contacts any of the selected points in the virtual model. In embodiments, responsive to determining that the incisal area contacts one or more of the selected points, the one or more selected points are removed from the selected points in the virtual model. For example, if an incisal area on tooth 6 were determined to overlap one or more of points 1617B, the one or more overlapping points of points 1617B would be removed from the selected points. Responsive to determining that an incisal area does not contact any of the selected points, the selected points are not removed.

Figure 17:
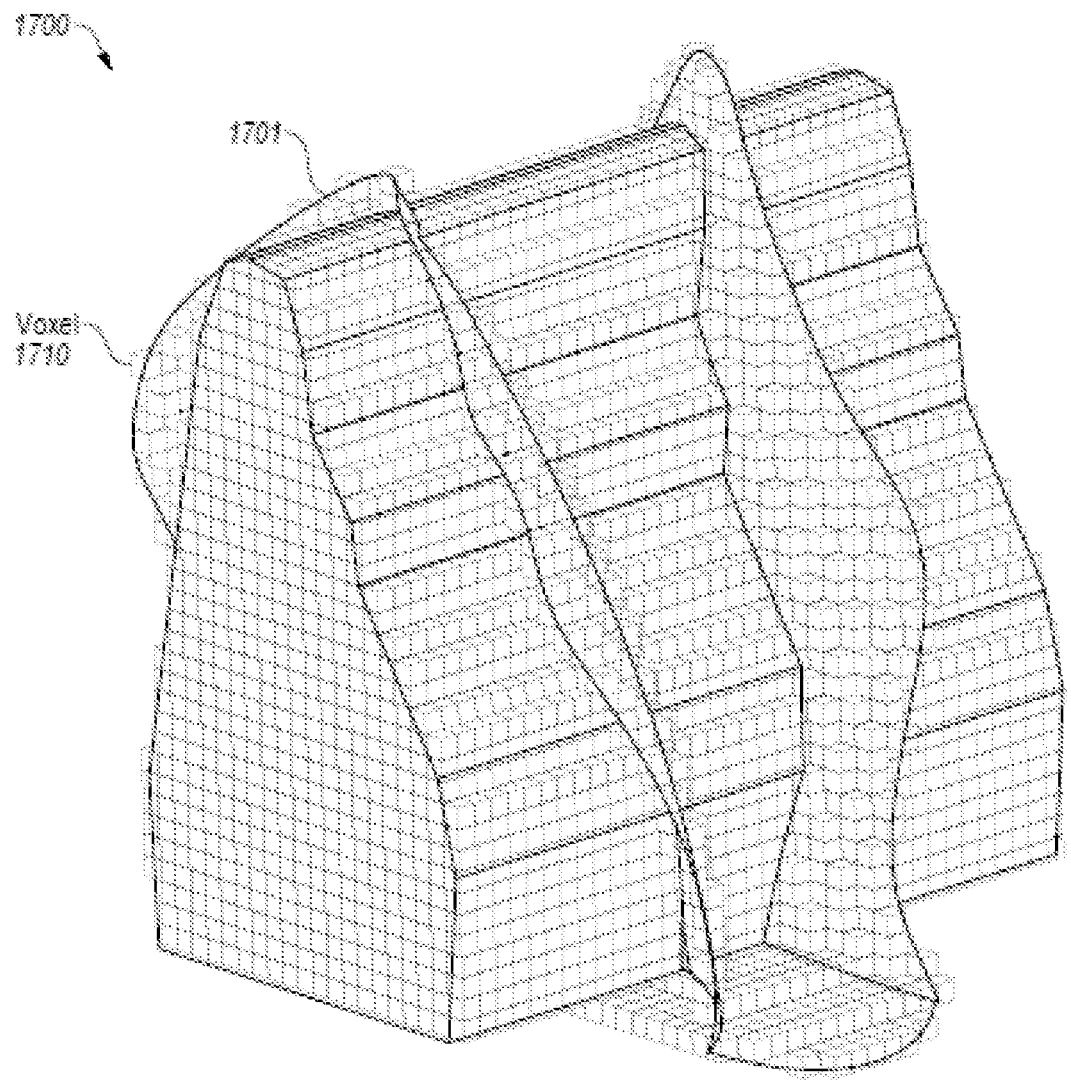
FIG. 17 illustrates a transformation of the selected point into a voxel volume, in accordance with some embodiments.

FIG. 17 illustrates a transformation of the selected set of points into a voxel volume, in accordance with some embodiments. In embodiments, the selected points as described above with respect to FIG. 16 are used to create another 3D object, such as a voxel volume. The voxel volume can be manipulated to smooth edges or corners of the 3D object. Diagram 1700 shows a voxel volume created from the selected points as described above with respect to FIG. 16. A voxel volume 1701 may refer to a volume or three-dimensional (3D) object that includes multiple voxels that fill the volume or 3D object. A voxel (also referred to as a "volumetric pixel" or "volume pixel" herein), such as voxel 1710, is the three-dimensional (3D) equivalent of a pixel. In embodiments, a voxel may be a polygon, such as a cube. In embodiments, a voxel may be the smallest distinguishable element of a 3D object, such as the voxel volume. In embodiments, a voxel can be a volume element that represents a specific grid value in 3D space. In embodiments, the selected points can be scalar values. A rasterization operation can be performed on the selected points. In embodiments, the rasterization operation transforms the selected points (e.g., scalar values) into voxels to create a voxel volume 1701. In some embodiments, the selected points can outline an outer surface of a voxel volume.

Performing the rasterization operation on the selected points creates a volumetric voxel surface and the rasterization process further fills the volumetric voxel surface with voxels to generate the voxel volume 1701.

FIGS. 18A-F illustrate a smoothing operation and polygonal mesh of the virtual filler, in accordance with some embodiments. In embodiments, the voxel volume, such as the voxel volume of FIG. 17 is manipulated in a smoothing operation so that the edges and corners are smoothed. FIG. A-E shows and respectively correspond to multiple stages (e.g., stages A-E) of a smoothing operation on a voxel volume. It may be noted that some or all the stages may be implemented in some embodiments. In embodiments, the smoothing operation smooths the voxel volume so that surface vertices (e.g., corners or edges) are smoothed to have a radius of curvature greater than a threshold amount. In some embodiments, the smoothing operation inflates and subsequently deflates the voxel volume to reduce corners or edges and increase the radius of curvature in the updated virtual filler. In some embodiments, after the smoothing operation is performed on the voxel volume, the resultant voxel volume can be further transformed into a scalar volumetric surface (e.g., polygonal mesh) where all surface vertices have a radius of curvature less than a threshold amount.

Figure 18A:
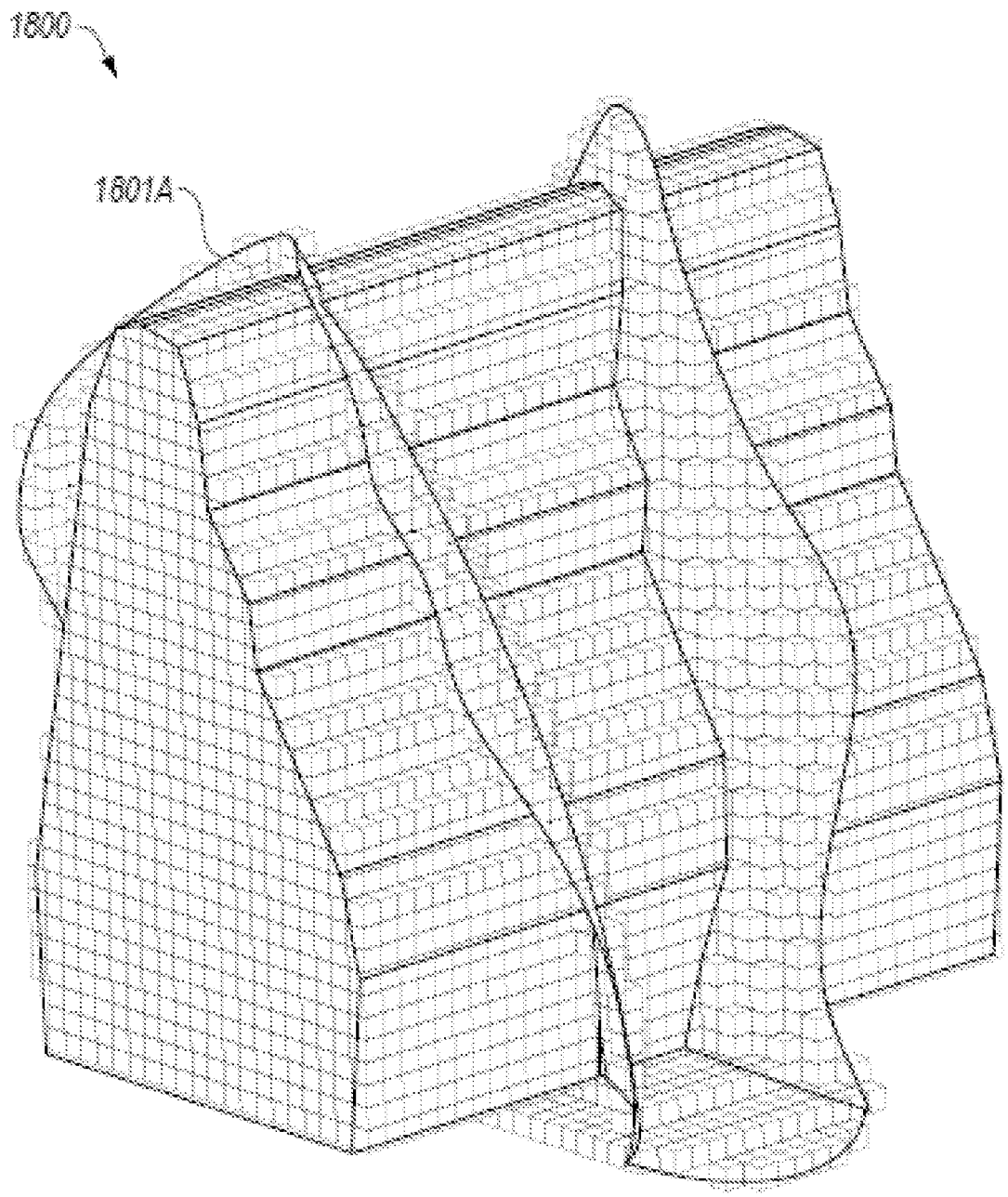
FIGS. 18A-F illustrate a smoothing operation and polygonal mesh of the virtual filler, in accordance with some embodiments.

In FIG. 18A at stage A, the voxel volume 1801A (e.g., initial voxel volume) is illustrated. Voxel volume 1801A may be the same or similar to voxel volume 1701 as described with respect to FIG. 17.

Figure 18B:
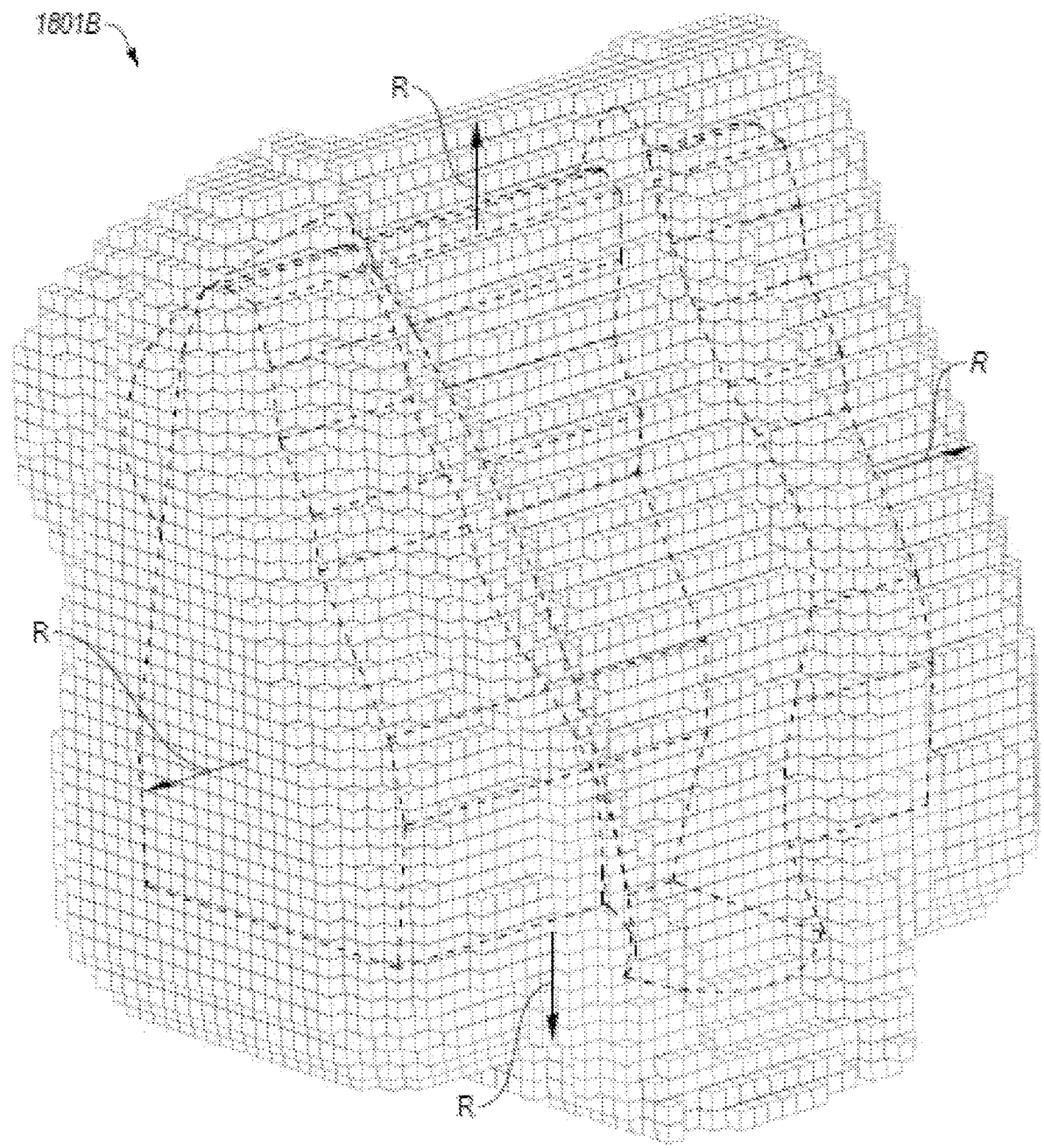

In FIG. 18B at stage B, the voxel volume 1801A is inflated (e.g., expanded) to generated an inflated voxel volume 1801B. In some embodiments, the surface of the voxel volume 1801A is inflated by a positive distance field offset (R) (also referred to as "voxel field" herein) to generate the inflated voxel volume 1801B. In embodiments, the positive distance field offset can be a distance along a line that is normal to the outer surface of the outer voxels of the voxel volume and that extends outward from the surface. Similarly, a negative distance field offset ($R^1$) can be a distance along a line that is normal to the outer surface of the outer voxels of the voxel volume and that extends inwards (into the voxel volume) from the surface. In embodiments, different distances for the distance field offset can be selected from a set of distances. As noted above, if more smoothing is desired (e.g., a larger radius of curvature for the surface virtual filler) a larger positive distance field offset can be used. Similarly if less smoothing is desired (e.g., a smaller radius of curvature for the surface virtual filler) a smaller positive distance field offset can be used.

In some embodiments, inflating the voxel volume 1801A may be performed by evaluating a distance of each voxel (voxels within the voxel volume 1801A and voxels outside the voxel volume 1801A (not shown)) from the surface (e.g., outer surface) of the voxel volume 1801A, and scoring each voxel based on the distance from the surface. Voxels on the surface of the voxel volume 1801A can have a low score (e.g., score of 0) and voxels away from the surface can have a higher score. The further away a voxel is from the surface of voxel volume 1801A the higher the score. As such, inflating a voxel volume 1801A by a positive distance field offset can be performed by selecting voxels having a particular score, which indicates that the voxels are a particular distance from the original surface of the voxel volume 1801A. The selected voxels having the particular score can become the outer surface of the inflated voxel volume 1801B.

Figure 18C:
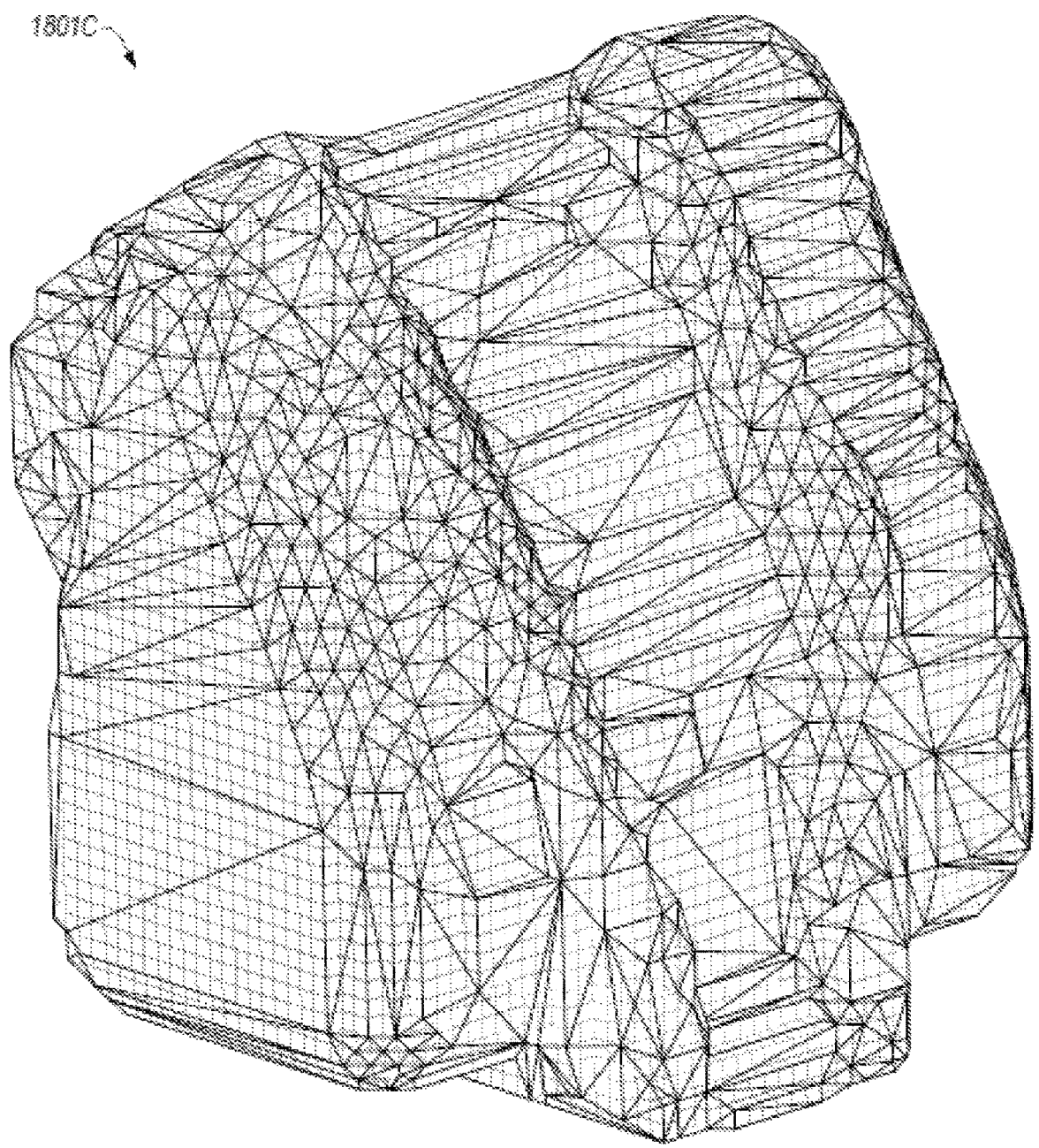

In FIG. 18C at stage C, the surface of the inflated voxel volume 1801B is transformed (also referred to as a "volume transformation operation" herein) into an inflated volumetric surface, such as polygonal mesh 1802, an example of which is a triangular mesh. The polygonal mesh can refer to multiple polygons that are linked or contact one another to form an outer surface of the 3D object. Transforming the inflated voxel volume 1801B can transform the voxels on the outer surface of the inflated voxel volume 1801B into one or polygons that are represented by scalar values. In embodiments, a volume transformation operation can be performed, such as a marching cubes operation that iteratively creates triangular surfaces for a 3D object. The volume transformation operation can "march" over all the voxels of voxel volume. The volume transformation operation determines whether a voxel has a vertex (e.g., corners) or an edge (e.g., where two sides of the voxel meet) that lie inside the voxel volume (e.g. not exposed to the voxel surface) and a vertex or an edge that is exposed to the surface of the voxel volume. If the volume transformation operation determines the above, the volume transformation operation transforms the voxel into one or more triangular surfaces. If the voxel's vertices and edges are entirely inside the voxel volume, the voxel is not transformed. If the voxel's vertices and edges are entirely outside the surface of the voxel volume, the voxel is not transformed.

Figure 18D:
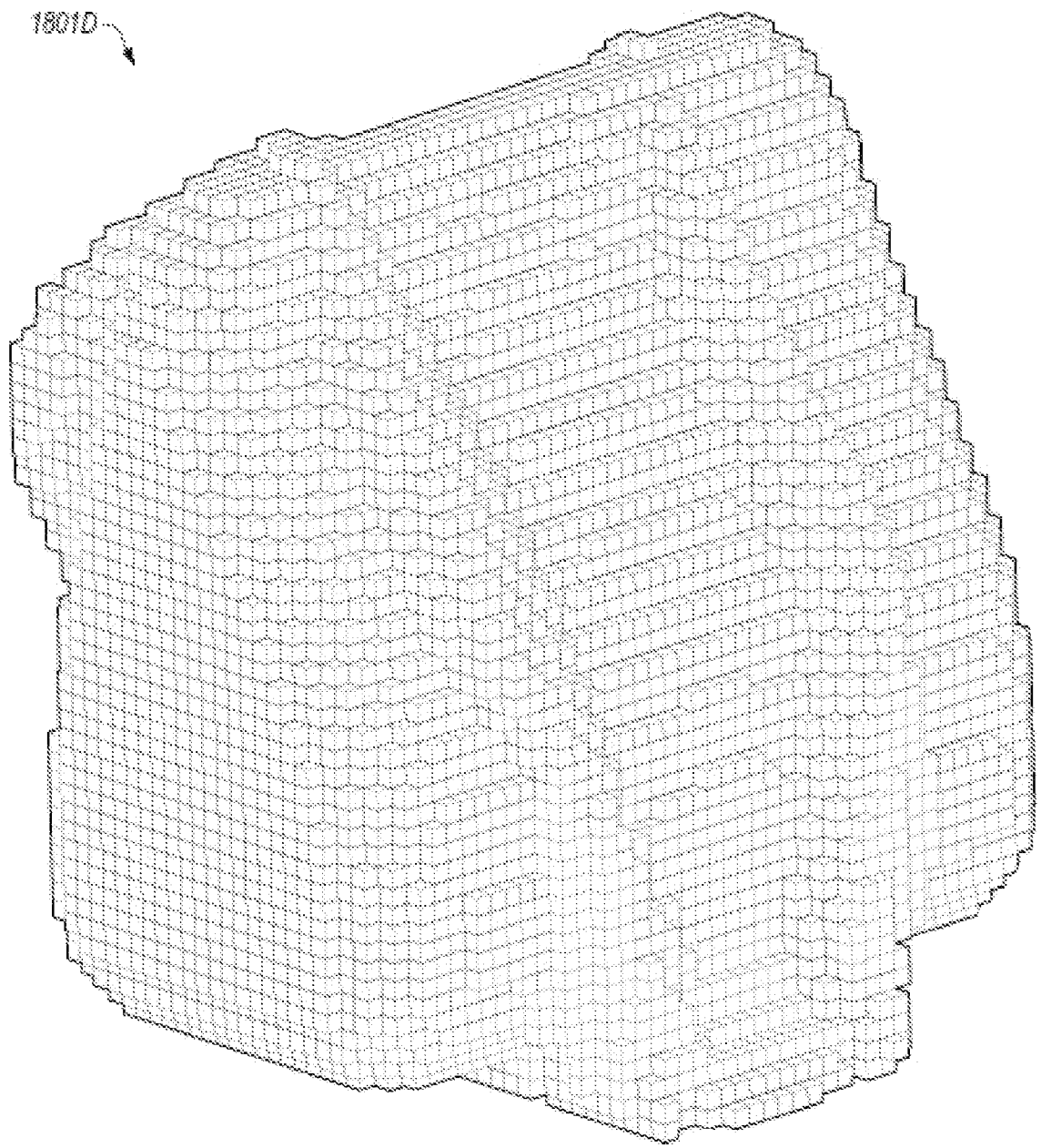

In FIG. 18D at stage D, the inflated polygonal mesh 1802 is transformed into an intermediate voxel volume 1801D. Similar as described with respect to FIG. 17, the scalar values of the polygonal mesh 1802 can be transformed into an intermediate voxel volume 1801D using a rasterization operation.

Figure 18E:
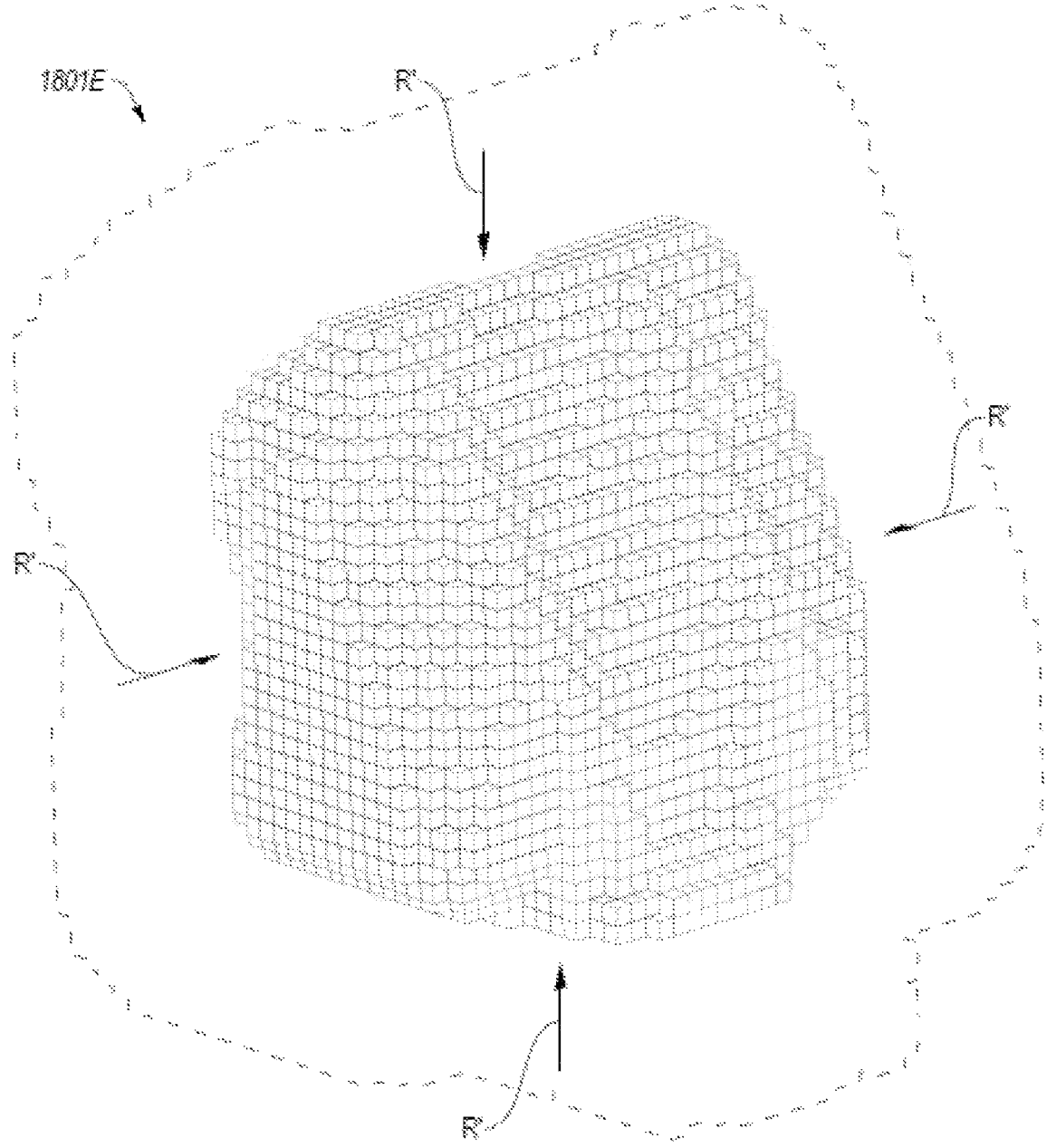
Figure 18F:
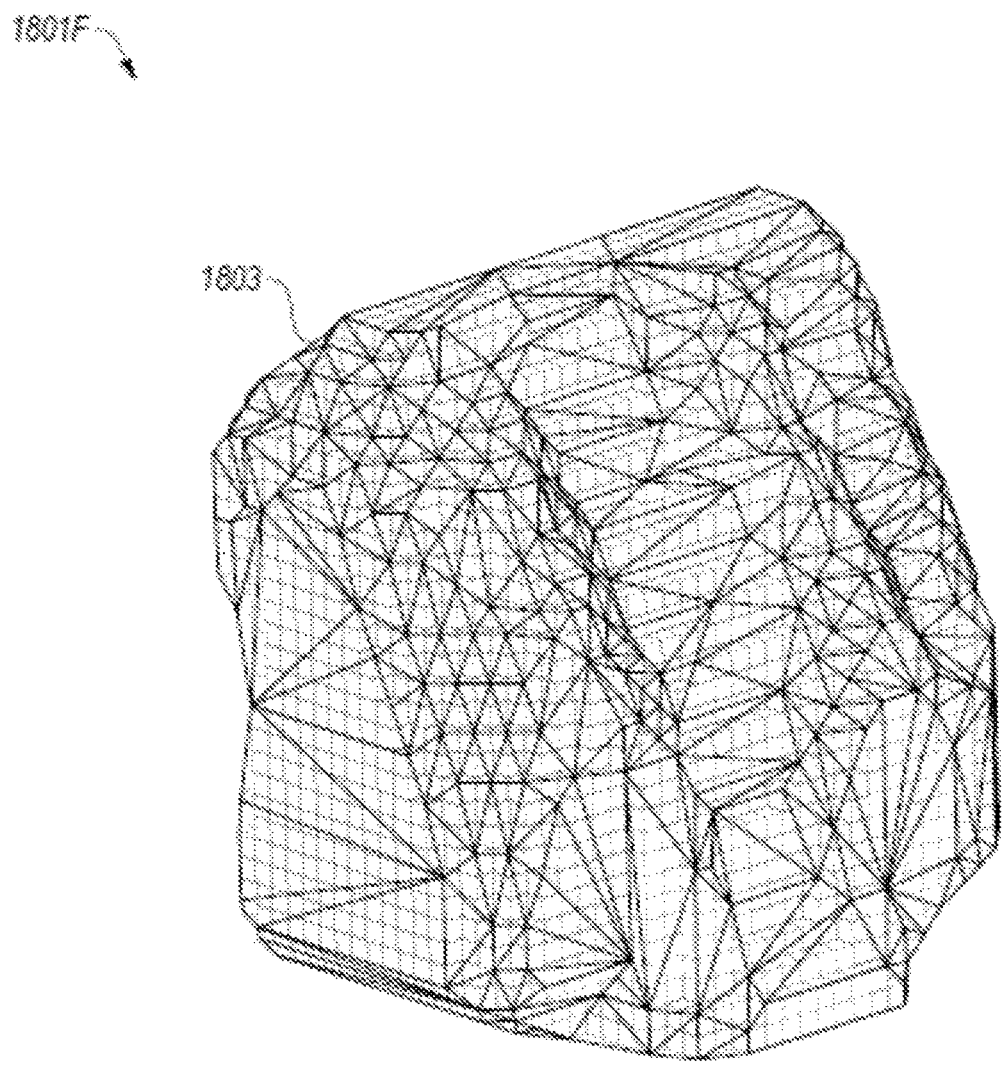

In FIG. 18E at stage E, the intermediate voxel volume 1801D can be deflated to generate a smoothed voxel volume 1801E. As illustrated, corners that existed in the initial voxel volume 1801A have been smoothed in the smoothed voxel volume 1801E. In some embodiments, deflating the intermediate voxel volume can be performed by using a negative distance field offset to generate the smoothed voxel volume 1801E, as described above with respect to stage B. In some embodiments, the negative distance field offset can be selected to be any distance. In an embodiment, the magnitude of the negative distance field offset is greater than the positive distance field offset that was initially used for inflation. By selecting a negative distance field offset that is greater in magnitude than the positive distance field offset, it can be ensured that the updated virtual filler is the same size or smaller than the initial virtual filler and fits within the adjacent teeth or crowded teeth (e.g., without the sides sticking out of at least one of the adjacent teeth or crowded teeth).

In implementations, in FIG. 18E at stage E can be an additional operation that is not considered part of the smoothing operation. Stage E is provided to illustrated an updated virtual filler 1803 based on the smoothing process. At stage E, subsequent to performing the smoothing operation, a geometry of the updated virtual filler 1803 can be determined by transforming the surface of the smoothed voxel volume 1801E into a polygonal mesh. The volume transformation operation at stage E is similar as described above with respect to stage C. In embodiments, the updated virtual filler 1803 can be included in an updated virtual model based on the determined geometry.

In embodiments, the geometry may include the 3D shape of the updated virtual filler 1803. In embodiments, the geometry may include the location of the updated virtual filler 1803 with respect to the teeth in the virtual model.

Figure 19A:
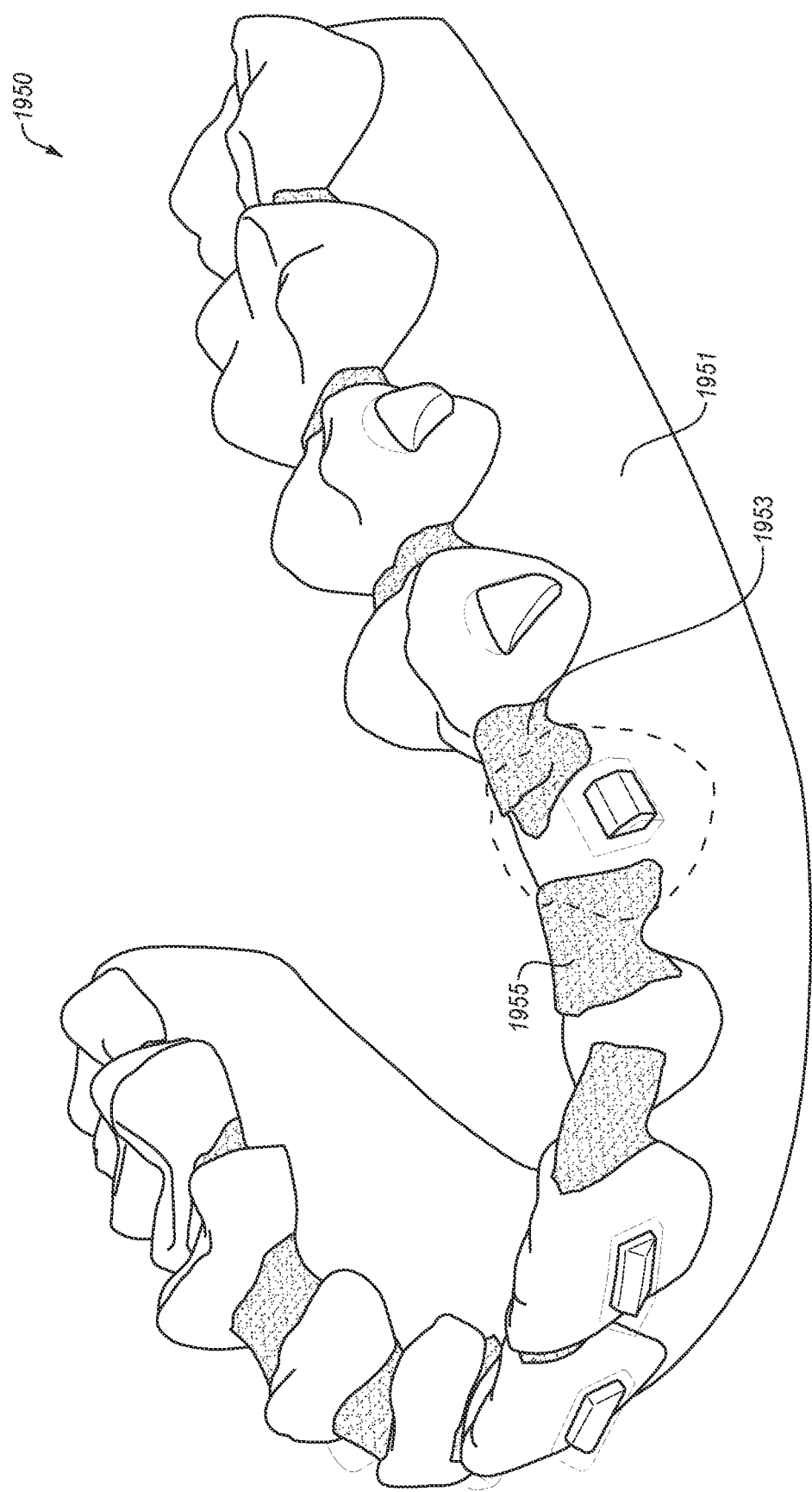
FIG. 19A illustrates a virtual model of a dental arch including updated virtual fillers, in accordance with embodiments or the disclosure.

FIG. 19A illustrates a virtual model of a dental arch including updated virtual fillers, in accordance with embodiments or the disclosure. Dental arch 1950 is a virtual model of a dental arch. Updated or final virtual fillers, such as virtual filler 1953 are disposed between adjacent teeth of the dental arch 1950. In embodiments, the virtual fillers of the dental arch have been generated using one or more operations described herein. Gingiva 1951 is shown included in dental arch 1950. Virtual filler 1955 is shown within part of the virtual filler within an adjacent tooth (right). For purposes of illustration, the tooth to the left of virtual filler 1955 is shown as missing.

Figure 19B:
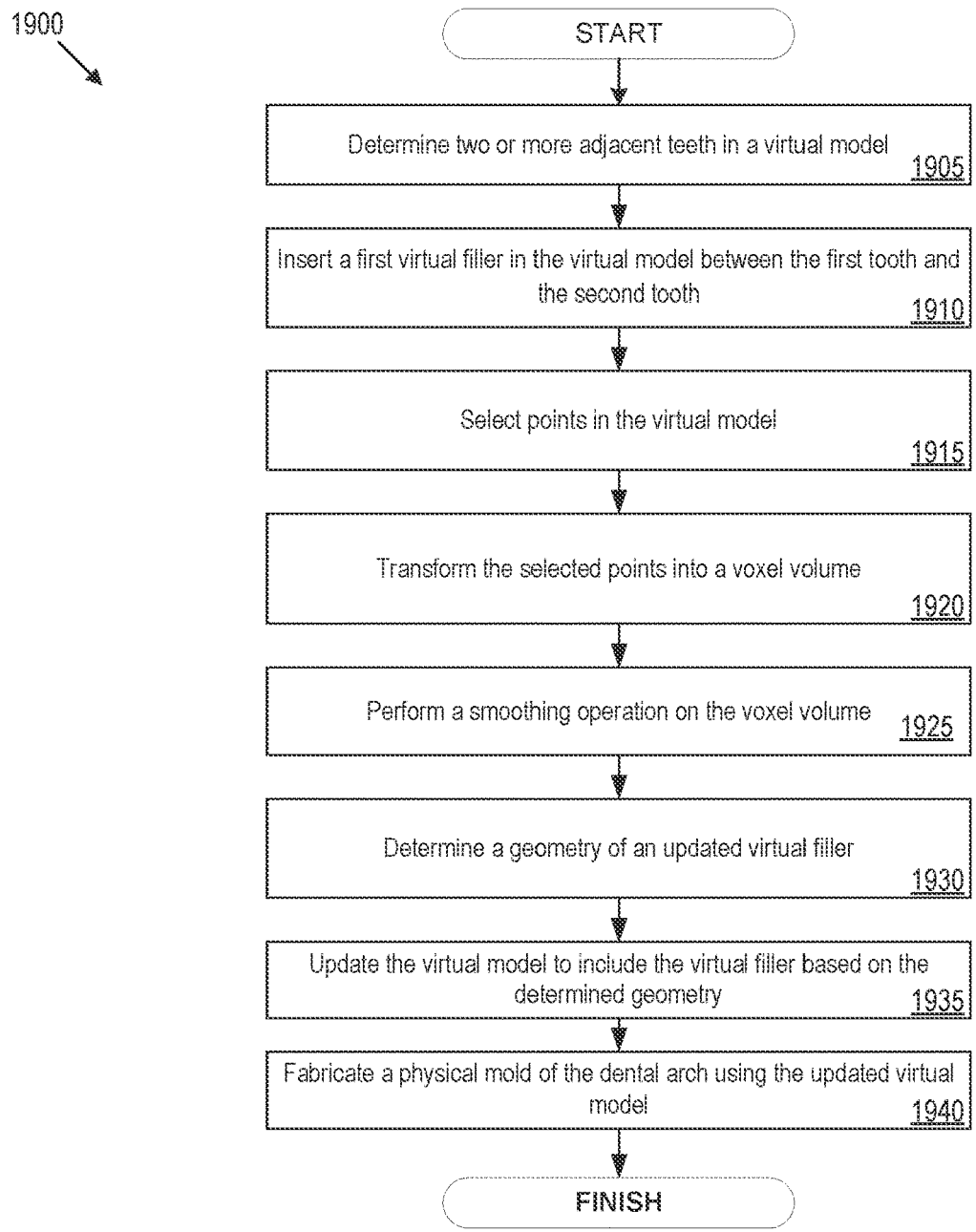
FIG. 19B illustrates a flow diagram for a method of creating a virtual filler for adjacent teeth or crowded teeth, in accordance with one embodiment.

FIG. 19B illustrates a flow diagram for a method of creating a virtual filler for adjacent teeth or crowded teeth, in accordance with one embodiment. One or more operations of method 1900 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 1900 may be performed by a processing device executing a computer aided drafting (CAD) program or module such as a virtual filler module 2050. Elements of the previous figures may be used to help illustrate method 1900. It may be appreciated that the in some implementations, method 1900 may include the same, different, fewer, or greater operations performed in any order.

In an embodiment, at block 1905 processing logic determines two or more adjacent teeth in a virtual model. The two or more adjacent teeth include a first tooth adjacent to a second tooth in the virtual model. In embodiments, processing logic can determine that the two or more adjacent teeth are adjacent teeth or crowded teeth, as described herein. Alternatively, no separate determination for crowded teeth may be performed. In embodiments, determining that the two or more adjacent teeth are adjacent teeth is performed as described herein above. In embodiments, determining that the two or more adjacent teeth includes determining at least three adjacent teeth in the virtual model satisfy a crowding criterion indicative of an amount of overlap between the teeth. The at least three adjacent teeth include the first tooth, the second tooth, and a third tooth.

At block 1910, processing logic inserts a first virtual filler (e.g., initial virtual filler) in the virtual model between the first tooth and the second tooth of two identified adjacent teeth. Inserting the first virtual filler is further described at least with respect to FIG. 15. In embodiments where the two or more adjacent teeth are crowded teeth, processing logic may insert a second virtual filler in the virtual model between the first tooth and a third tooth. Processing logic may also insert a third virtual filler in the virtual model between the second tooth and the third tooth.

At block 1915, processing logic selects points in the virtual model. In embodiments, the selected points include first points on a surface of the first tooth. In embodiments, the selected points include second points on a surface of the second tooth. In embodiments, the selected points include third points on a surface of gingiva. In embodiments, the selected points include fourth points on the first virtual filler. In the case of crowded teeth, the selected points may also include points on a third tooth. In embodiments, selecting the first points on the surface of the first tooth includes selecting points on the surface of the first tooth that are within a threshold distance from at least one of the first virtual filler or the surface of the second tooth (and optionally the surface of the first tooth in the case of crowded teeth). It can be noted that a similar selection of points on the surface of a tooth can be performed for any of the teeth in the adjacent teeth or crowded teeth. In embodiments, selecting the third points on the surface of the gingiva includes selecting points on the surface of the gingiva that are within a threshold distance from the first virtual filler. It can also be noted that a similar selection of points on the surface of the gingiva can be performed for any other virtual fillers, such as additional virtual fillers used with crowded teeth. In embodiments where the two or more adjacent teeth are determined to be crowded teeth, the selected points in the virtual model include fifth points on a surface of the third tooth, sixth points on the second virtual filler, and seventh points on the third virtual filler.

In some embodiments, the first virtual filler in the virtual model inserted between the first tooth and the second tooth is a virtual filler of a predetermined shape. In some embodiments, any of the virtual fillers inserted between the teeth of crowded teeth can be of a predetermined shape. In some embodiments, any of the virtual fillers inserted between the teeth of crowded teeth can be of a different predetermined shape. In some embodiments, the first virtual filler (or any of the virtual fillers) include a first side and a second side. In embodiments, the first side of the first virtual filler is located within the first tooth and the second side of the first virtual filler is located within the second tooth. In other embodiments, the first virtual filler (or any virtual filler) is not a predetermined shape but generated using operations described herein.

At block 1920, processing logic transforms the selected points into a voxel volume that includes multiple voxels. A rasterization process that transforms the selected points into a voxel volume is further described at least with respect to FIG. 18.

At block 1925, processing logic performs a smoothing operation on the voxel volume to generate a smoothed voxel volume. In an embodiment, to perform the smoothing operation on the voxel volume, processing logic inflates the voxel volume by a first distance field offset to generate an inflated voxel volume. In an embodiment, to perform the smoothing operation on the voxel volume, processing logic transforms a surface of the inflated voxel volume into an inflated polygonal mesh. In an embodiment, to perform the smoothing operation on the voxel volume, processing logic transforms the inflated polygonal mesh into an intermediate voxel volume. In an embodiment, to perform the smoothing operation on the voxel volume, processing logic deflates the intermediate voxel volume by a second distance field offset to generate the smoothed voxel volume. In an embodiment, the second distance field offset is greater in magnitude than the first distance field offset. In embodiments, a smoothing operation is performed as described above with reference to FIG. 18.

At block 1930, subsequent to performing the smoothing operation on the voxel volume, processing logic determines a geometry of an updated virtual filler. In embodiments, processing logic determines a geometry of an updated virtual filler by transforming a surface of the smoothed voxel volume into a polygonal mesh. Transforming a surface of the smoothed voxel volume into a polygonal mesh is further described at least with respect to FIG. 18.

At block 1935, processing logic updates the virtual model to include the virtual filler based on the determined geometry. In embodiments, the virtual model is a model of a dental arch. At block 1940, processing logic fabricates a physical mold of the dental arch using the updated virtual model. The physical mold includes material in an area of the updated virtual filler.

FIG. 20 illustrates a diagrammatic representation of a machine in the example form of a computing device within which a set of instructions, for causing the machine to perform any one or more of the methodologies discussed with reference to the methods 600, 1200, 1300, or 1900 of FIG. 6A-B, 12, 13, or 19, respectively. In embodiments, the machine may be connected (e.g., networked) to other machines in a Local Area Network (LAN), an intranet, an extranet, or the Internet. For example, the machine may be networked to a rapid prototyping apparatus such as a 3D printer or SLA apparatus. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computing device 2000 includes a processing device 2002, a main memory 2004 (e.g., read-only memory (ROM), flash memory, dynamic random access memory (DRAM) such as synchronous DRAM (SDRAM), etc.), a static memory 2006 (e.g., flash memory, static random access memory (SRAM), etc.), and a secondary memory (e.g., a data storage device 2028), which communicate with each other via a bus 2008. Static memory 2006, main memory 2004, or a combination there of may also be referred to as a memory device herein.

Processing device 2002 represents one or more general-purpose processors such as a microprocessor, central processing unit, or the like. More particularly, the processing device 2002 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 2002 may also be one or more special-purpose processing devices such as an application specific integrated circuit (ASIC), a field programmable gate array (FPGA), a digital signal processor (DSP), network processor, or the like. Processing device 2002 is configured to execute the processing logic (instructions 2026) for performing operations discussed herein.

The computing device 2000 may further include a network interface device 2022 for communicating with a network 2064. The computing device 2000 also may include a video display unit 2010 (e.g., a liquid crystal display (LCD) or a cathode ray tube (CRT)), an alphanumeric input device 2012 (e.g., a keyboard), a cursor control device 2014 (e.g., a mouse), and a signal generation device 2020 (e.g., a speaker).

The data storage device 2028 may include a machine-readable storage medium (or more specifically a non-transitory computer-readable storage medium) 2024 on which is stored one or more sets of instructions 2026 embodying any one or more of the methodologies or functions described herein. A non-transitory storage medium refers to a storage medium other than a carrier wave. The instructions 2026 may also reside, completely or at least partially, within the main memory 2004 and/or within the processing device 2002 during execution thereof by the computer device 2000, the main memory 2004 and the processing device 2002 also constituting computer-readable storage media.

The computer-readable storage medium 2024 may also be used to store one or more virtual 3D models (also referred to as electronic models) and/or a virtual filler module 2050, which may perform one or more of the operations of methods 600, 1200, 1300, or 1900 described with reference to FIGS. 6A-B, 12, 13, or 19. The computer readable storage medium 2024 may also store a software library containing methods that call a virtual filler module 2050. While the computer-readable storage medium 2024 (e.g., non-transitory computer readable storage medium) is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing or encoding a set of instructions for execution by the machine and that cause the machine to perform any one or more of the methodologies of the present disclosure. The term "computer-readable storage medium" shall accordingly be taken to include, but not be limited to, solid-state memories, and optical and magnetic media.

In the foregoing description, numerous details are set forth. It will be apparent, however, to one of ordinary skill in the art having the benefit of this disclosure, that the present disclosure may be practiced without these specific details. In some instances, well-known structures and devices are shown in block diagram form, rather than in detail, in order to avoid obscuring the present disclosure.

Some portions of the detailed description have been presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of operations leading to a result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It may be borne in mind, however, that all of these and similar terms are to be associated with the appropriate physical quantities and are merely convenient labels applied to these quantities. Unless specifically stated otherwise, it is appreciated that throughout the description, discussions utilizing terms such as "detecting," "updating," "determining," "fabricating," "removing," "modifying," "simulating," "projecting," "connecting," or the like, refer to the actions and processes of a computer system, or similar electronic computing device, that manipulates and transforms data represented as physical (e.g., electronic) quantities within the computer system memories or registers into other data similarly represented as physical quantities within the computer system memories or registers or other such information storage, transmission or display devices.

The present disclosure also relates to an apparatus for performing the operations herein. This apparatus may be specially constructed for the required purposes, or it may include a general purpose computer selectively activated or reconfigured by a computer program stored in the computer. Such a computer program may be stored in a computer readable storage medium, such as, but not limited to, any type of disk including a floppy disk, an optical disk, a compact disc read-only memory (CD-ROM), a magnetic-optical disk, a read-only memory (ROM), a random access memory (RAM), an erasable programmable read-only memory (EPROM), an electrically erasable programmable read-only memory (EEPROM), a magnetic or optical card, or any type of media suitable for storing electronic instructions.

The words "example" or "exemplary" are used herein to mean serving as an example, instance, or illustration. Any aspect or design described herein as "example' or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or." That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims may generally be construed to mean "one or more" unless specified otherwise or clear from context to be directed to a singular form. Moreover, use of the term "an implementation" or "one implementation" or "an implementation" or "one implementation" throughout is not intended to mean the same implementation or implementation unless described as such. The terms "first," "second," "third," "fourth," etc. as used herein are meant as labels to distinguish among different elements and may not necessarily have an ordinal meaning according to their numerical designation.

It is to be understood that the above description is intended to be illustrative, and not restrictive. Many other embodiments will be apparent upon reading and understanding the above description. Although embodiments of the present disclosure have been described with reference to specific example embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

What is claimed is:

1. A method for generating a virtual filler for design of an orthodontic aligner, comprising:
   inserting the virtual filler in a virtual model of a dental site between a first tooth and a second tooth in the virtual model, the inserted virtual filler having a predetermined three-dimensional shape irrespective of a user manipulation, wherein one or more of the first tooth or the second tooth represent a natural tooth of a patient;
   transforming a plurality of points of the first tooth, the second tooth and the virtual filler into a voxel volume; and
   determining, by a processing device, a geometry of an updated virtual filler by transforming a surface of the voxel volume into a polygonal mesh.

2. The method of claim 1, further comprising:
   determining two or more adjacent teeth in the virtual model, the two or more adjacent teeth comprising the first tooth adjacent to the second tooth in the virtual model; and
   selecting the plurality of points.

3. The method of claim 2, wherein determining the two or more adjacent teeth in the virtual model comprises:
   determining that the two or more adjacent teeth comprise at least three adjacent teeth in the virtual model that satisfy a crowding criterion indicative of an amount of overlap between the at least three adjacent teeth, wherein the at least three adjacent teeth comprise the first tooth, the second tooth, and a third tooth.

4. The method of claim 3, wherein the virtual filler is a first virtual filler, the method further comprising:
   inserting a second virtual filler in the virtual model between the first tooth and the third tooth; and
   inserting a third virtual filler in the virtual model between the second tooth and the third tooth.

5. The method of claim 1, wherein the plurality of points comprise first points on a surface of the first tooth, second points on a surface of the second tooth, third points on a surface of gingiva, and fourth points on the virtual filler.

6. The method of claim 5, wherein:
   selecting the first points on the surface of the first tooth comprises selecting points on the surface of the first tooth that are within a threshold distance from at least one of the virtual filler or the surface of the second tooth; and
   selecting the third points on the surface of the gingiva comprises selecting points on the surface of the gingiva that are within the threshold distance of the virtual filler.

7. The method of claim 1, further comprising:
   performing a smoothing operation on the voxel volume.

8. The method of claim 7, wherein performing the smoothing operation on the voxel volume comprises:
   inflating the voxel volume by a first distance field offset to generate an inflated voxel volume;
   transforming a surface of the inflated voxel volume into an inflated polygonal mesh;
   transforming the inflated polygonal mesh into an intermediate voxel volume; and
   deflating the intermediate voxel volume by a second distance field offset to generate a smoothed voxel volume.

9. The method of claim 8, wherein the second distance field offset is greater than the first distance field offset.

10. The method of claim 1, wherein the virtual filler comprises a first side and a second side, the first side of the virtual filler located within the first tooth, the second side of the virtual filler located within the second tooth.

11. The method of claim 1, wherein the dental site comprises a dental arch, the method further comprising:
    updating the virtual model to include the updated virtual filler based on the determined geometry.

12. The method of claim 11, further comprising:
    fabricating a physical mold of the dental arch using the updated virtual model, wherein the physical mold comprises material in an area of the updated virtual filler.

13. A system for generating a virtual filler for design of an orthodontic aligner, comprising:
- a memory device; and
- a processing device operatively coupled to the memory device, the processing device to:
- insert the virtual filler in a virtual model of a dental site between a first tooth and a second tooth in the virtual model, the inserted virtual filler having a predetermined three-dimensional shape irrespective of a user manipulation, wherein one or more of the first tooth or the second tooth represent a natural tooth of a patient;
- transform a plurality of points of the first tooth, the second tooth and the virtual filler into a voxel volume; and
- determine a geometry of an updated virtual filler by transforming a surface of the voxel volume into a polygonal mesh.

14. The system of claim 13, the processing device further to:
- determine two or more adjacent teeth in the virtual model, the two or more adjacent teeth comprising the first tooth adjacent to the second tooth in the virtual model; and
- select the plurality of points.

15. The system of claim 13, wherein the virtual model is a virtual model of a dental arch, the processing device further to:
- update the virtual model to include the updated virtual filler based on the determined geometry.

16. The system of claim 15, the processing device further to:
- fabricate a physical mold of the dental arch using the updated virtual model, wherein the physical mold comprises material in an area of the updated virtual filler.

17. A non-transitory computer-readable medium comprising instructions for generating a virtual filler for design of an orthodontic aligner that, responsive to execution by a processing device, cause the processing device to perform operations comprising:
- inserting the virtual filler in a virtual model of a dental site between a first tooth and a second tooth in the virtual model, the inserted virtual filler having a predetermined three-dimensional shape irrespective of a user manipulation, wherein one or more of the first tooth or the second tooth represent a natural tooth of a patient;
- transforming a plurality of points of the first, the second tooth and the virtual filler into a voxel volume; and
- determining, by the processing device, a geometry of an updated virtual filler by transforming a surface of the voxel volume into a polygonal mesh.

18. The non-transitory computer-readable medium of claim 17, the operations further comprising:
- determining two or more adjacent teeth in the virtual model, the two or more adjacent teeth comprising the first tooth adjacent to the second tooth in the virtual model; and
- selecting the plurality of points.

19. The non-transitory computer-readable medium of claim 17, wherein the dental site comprises a dental arch, the operations further comprising:
- updating the virtual model to include the updated virtual filler based on the determined geometry.

20. The non-transitory computer-readable medium of claim 19, the operations further comprising
- fabricating a physical mold of the dental arch using the updated virtual model, wherein the physical mold comprises material in an area of the updated virtual filler.

* * * * *